US009953128B2

(12) United States Patent
Maruyama et al.

(10) Patent No.: US 9,953,128 B2
(45) Date of Patent: Apr. 24, 2018

(54) IDENTIFICATION APPARATUS, CONTROL APPARATUS, IDENTIFICATION METHOD, PROGRAM, AND IDENTIFICATION SYSTEM

(71) Applicant: Sony Corporation, Tokyo (JP)

(72) Inventors: Takao Maruyama, Kanagawa (JP); Masakazu Yajima, Kanagawa (JP); Munekatsu Fukuyama, Tokyo (JP); Yohei Fukuma, Chiba (JP)

(73) Assignee: Sony Corporation, Tokyo (JP)

( * ) Notice: Subject to any disclaimer, the term of this patent is extended or adjusted under 35 U.S.C. 154(b) by 1154 days.

(21) Appl. No.: 13/670,559

(22) Filed: Nov. 7, 2012

(65) Prior Publication Data
US 2013/0124120 A1    May 16, 2013

(30) Foreign Application Priority Data

Nov. 14, 2011    (JP) ................. 2011-248685

(51) Int. Cl.
| | | |
|---|---|---|
| *G06F 19/00* | (2011.01) | |
| *G01R 21/00* | (2006.01) | |
| *G06Q 50/06* | (2012.01) | |
| *A61B 5/16* | (2006.01) | |
| *A61B 5/00* | (2006.01) | |

(52) U.S. Cl.
CPC .............. *G06F 19/00* (2013.01); *A61B 5/167* (2013.01); *G01R 21/00* (2013.01); *G06Q 50/06* (2013.01); *A61B 5/0002* (2013.01); *A61B 2560/0214* (2013.01); *A61B 2560/0242* (2013.01)

(58) Field of Classification Search
CPC ......... G01R 21/00; G06F 19/00; G06F 17/00; G06Q 50/06; A61B 5/117; A61B 5/15136; A61B 5/167; A61B 2560/0214; A61B 2560/0223; A61B 2560/0242; A61B 2560/0257; A61B 2560/0295; A61B 5/0002
USPC ............................................. 702/60, 61, 63
See application file for complete search history.

(56) References Cited

U.S. PATENT DOCUMENTS

| | | | | |
|---|---|---|---|---|
| 8,333,641 | B2* | 12/2012 | Sullivan ............ | A63F 13/12 463/10 |
| 8,949,070 | B1* | 2/2015 | Kahn ................ | G01C 22/006 702/141 |
| 2011/0133688 | A1* | 6/2011 | Ishibashi ................ | 320/101 |
| 2011/0231542 | A1* | 9/2011 | Komano et al. ......... | 709/224 |

(Continued)

FOREIGN PATENT DOCUMENTS

| | | |
|---|---|---|
| CN | 101549205 A | 10/2009 |
| JP | 2000-084137 A | 3/2000 |

(Continued)

OTHER PUBLICATIONS

Francesco Cottone, Introduction to Vibration Energy Harvesting, 2011.*

*Primary Examiner* — Sujoy Kundu
*Assistant Examiner* — Lynda Dinh
(74) *Attorney, Agent, or Firm* — Wolf, Greenfield & Sacks, P.C.

(57) ABSTRACT

Disclosed is an identification apparatus including an acquisition unit configured to acquire power generation information from a power generation unit; and an identification unit configured to identify a behavior characteristic in accordance with the power generation information.

15 Claims, 17 Drawing Sheets

(56) References Cited

U.S. PATENT DOCUMENTS

2012/0129603 A1* 5/2012 Song .................. A63F 13/24
                                                    463/36
2013/0024045 A1* 1/2013 Fujiwara et al. ............. 700/297

FOREIGN PATENT DOCUMENTS

| JP | 2000-167233 A | 6/2000 |
| --- | --- | --- |
| JP | 2005-151271 A | 6/2005 |
| JP | 2009-022440 A | 2/2009 |
| JP | 2011-518360 A | 6/2011 |

* cited by examiner

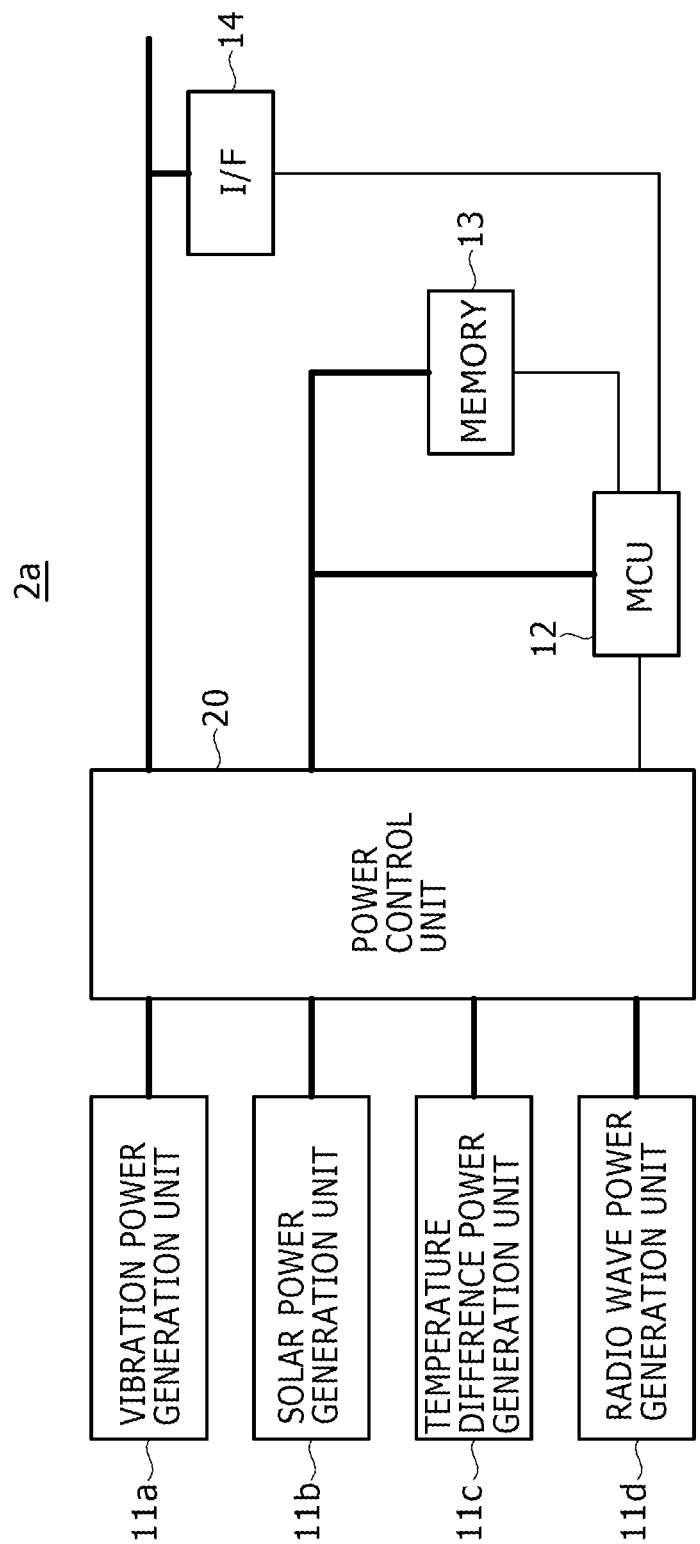

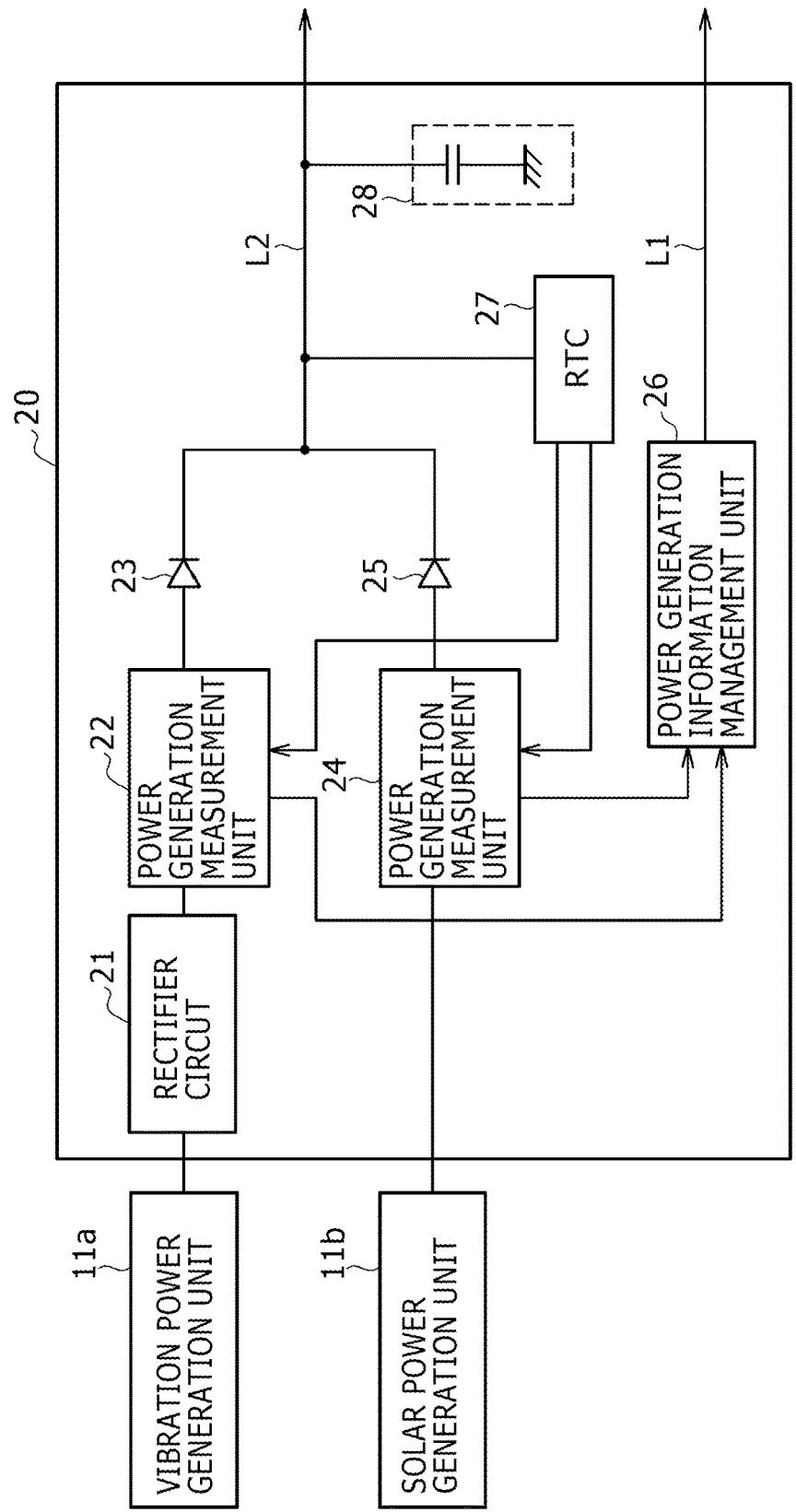

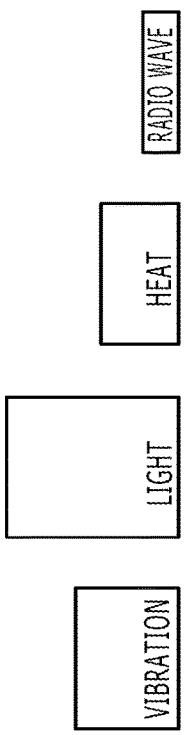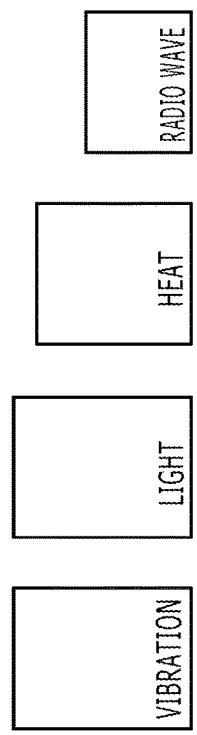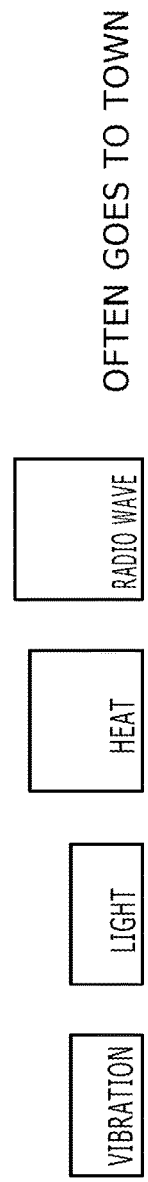

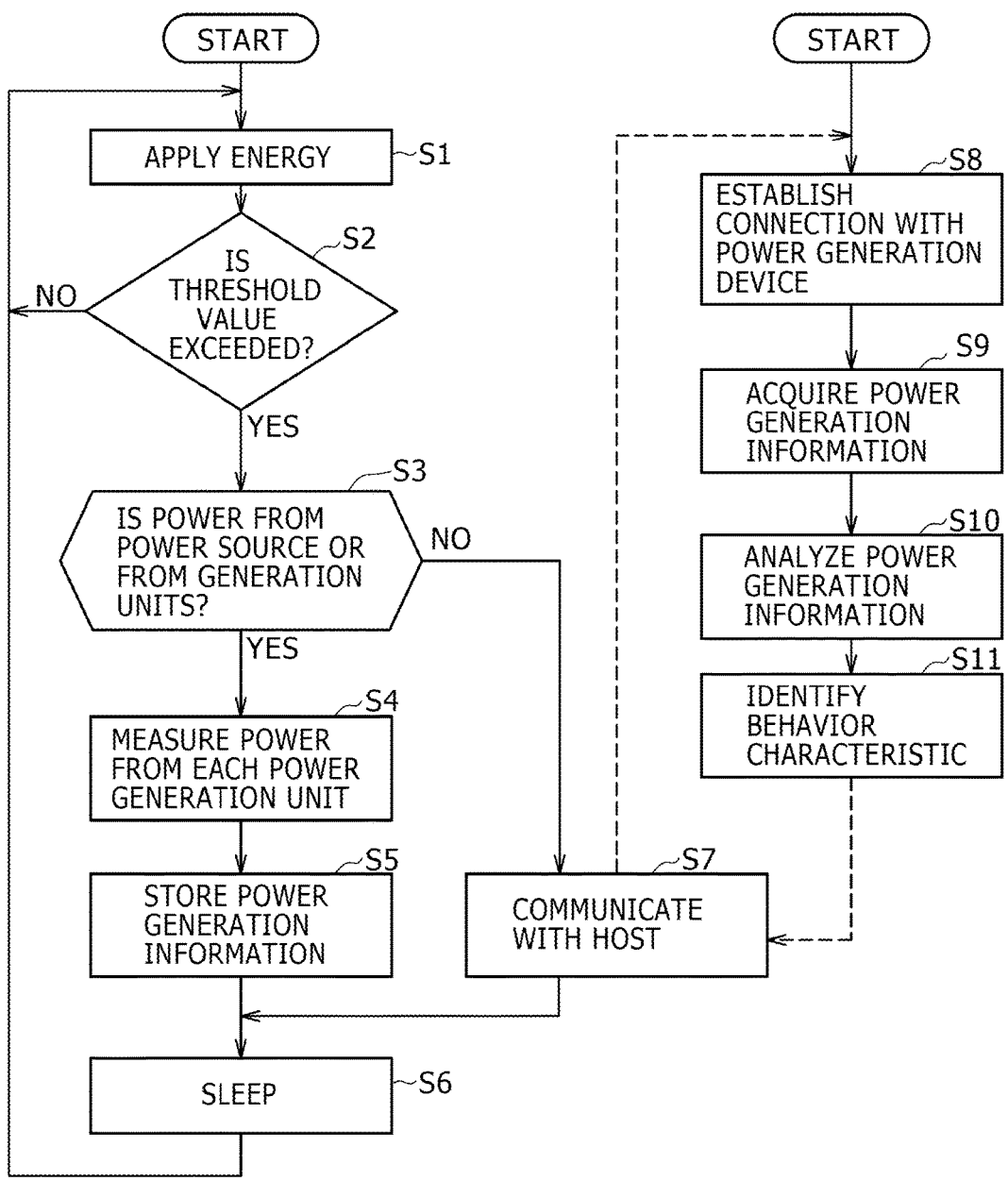

|  | POWER GENERATION INFORMATION | | | | BEHAVIOR CHARACTERISTICS | CHARACTERS |
| --- | --- | --- | --- | --- | --- | --- |
|  | 11a | 11b | 11c | 11d | | |
| FIG. 6A | VIBRATION | LIGHT | HEAT | RADIO WAVE | ENJOYS OUTDOOR ACTIVITIES | CHARACTER LIVING IN THE MOUNTAINS |
| FIG. 6B | VIBRATION | LIGHT | HEAT | RADIO WAVE | ENJOYS DOING SPORTS | STURDY WARRIOR |
| FIG. 6C | VIBRATION | LIGHT | HEAT | RADIO WAVE | MOSTLY STAYS INDOORS | WITCH DRESSED IN BLACK |
| FIG. 6D | VIBRATION | LIGHT | HEAT | RADIO WAVE | OFTEN GOES TO TOWN | MISCHIEVOUS DWARF |

F I G . 7

| CHARACTER ID | CHARACTER NAME | GENDER | HOLINESS | VOID | DARKNESS | WIND | FIRE | WATER | EARTH |
|---|---|---|---|---|---|---|---|---|---|
| 00A021A0 | ○○ | 00 | 40 | 10 | 25 | 10 | 40 | 100 | 0 |
| H8101622 | ▲▲○× | 01 | 30 | 40 | 100 | 0 | 100 | 50 | 50 |
| ⋮ | ⋮ | ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ | ⋮ | ⋮ |

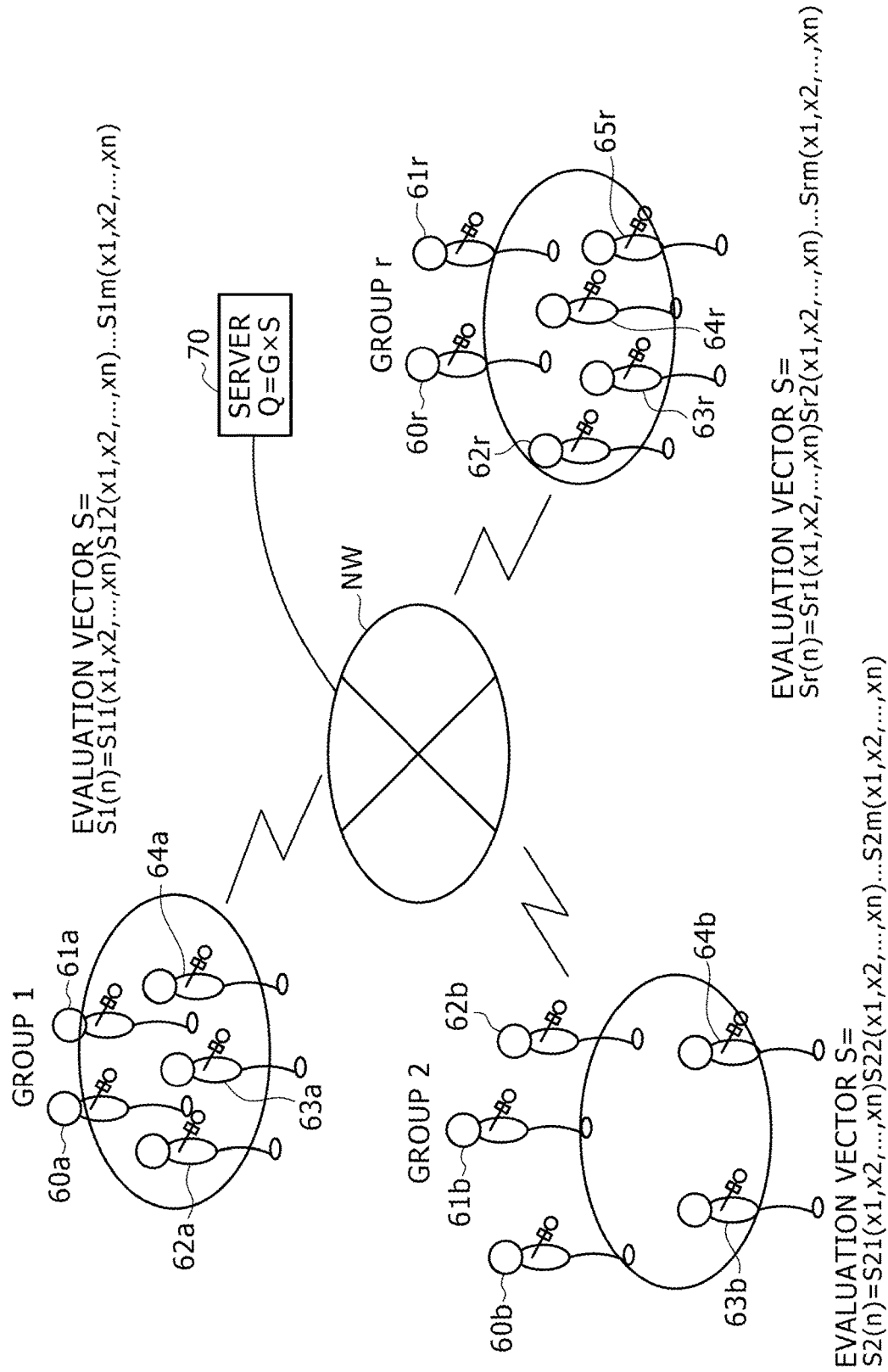

IDENTIFICATION APPARATUS, CONTROL APPARATUS, IDENTIFICATION METHOD, PROGRAM, AND IDENTIFICATION SYSTEM

CROSS REFERENCE TO RELATED APPLICATION

This application claims the priority benefit of Japanese Patent Application JP 2011-248685 filed in the Japanese Patent Office on Nov. 14, 2011, the entire content of which is hereby incorporated by reference.

BACKGROUND

The present disclosure relates to an identification apparatus, a control apparatus, an identification method, a program, and an identification system for identifying the behavior characteristic of a user in accordance with power generation information from, for example, a solar power generation unit or a vibration power generation unit.

With health awareness on the rise, there are dedicated sensors which a user wears to measure his or her amount of exercise. In recent years, to let users enjoy exercising, systems that associate exercise amount with video games have been proposed. For example, Japanese Patent Laid-open No. 2009-22440 (Patent Document 1) discloses a system where an exercise amount gauge is attached to a user's waist to measure the user's amount of exercise, and video game parameters are set in accordance with the measured results.

SUMMARY

The exercise amount gauge described in Patent Document 1 is driven generally using a battery such as a dry cell or button battery as its power source. This is disadvantageous because the remaining capacity of the battery needs to be checked constantly and the battery needs to be replaced as required. Another disadvantage is that when the remaining capacity of the battery becomes low, the exercise amount gauge stops operation and the amount of exercise will not be recorded, and since the amount of exercise is not recorded, it will not be reflected to the video game parameters. In addition, a dedicated sensor for measuring the amount of exercise has to be provided.

It is therefore desirable to provide an identification apparatus, a control apparatus, an identification method, a program, and an identification system capable of acquiring information to be reflected in, say, a virtual object without using a battery or a sensor.

According to one embodiment of the present disclosure, there is provided an identification apparatus including an acquisition unit configured to acquire power generation information from a power generation unit; and an identification unit configured to identify a behavior characteristic in accordance with the power generation information.

According to another embodiment of the present disclosure, there is provided a control apparatus including an acquisition unit configured to acquire power generation information from a power generation unit; and an attribute processing unit configured to have the power generation information reflected in an attribute of a virtual object.

According to another embodiment of the present disclosure, there is provided an identification method for an identification apparatus, the identification method including: acquiring power generation information from a power generation unit in the identification apparatus; and identifying a behavior characteristic in accordance with the power generation information.

According to another embodiment of the present disclosure, there is provided a program for causing a computer to execute an identification method including: acquiring power generation information from a power generation unit; and identifying a behavior characteristic in accordance with the power generation information.

According to another embodiment of the present disclosure, there is provided an identification system having a plurality of identification apparatuses each including an acquisition unit configured to acquire power generation information from a power generation unit, and an identification unit configured to identify a behavior characteristic in accordance with the power generation information. The identification system acquires the power generation information from each of the identification apparatuses, and identifies a behavior characteristic on a group basis in accordance with the pieces of power generation information.

According to at least one of the embodiments of this disclosure, it is possible to acquire information to be reflected in a virtual object without using a battery or a sensor. This information may be the behavior characteristic of a user, for example.

BRIEF DESCRIPTION OF THE DRAWINGS

FIG. 2 is a block diagram showing a typical structure of a power generation device in a first embodiment of this disclosure;

FIG. 3 is a block diagram showing a typical structure of a power control unit;

FIGS. 4A through 4D are schematic views showing examples of relations between power generation information and behavior characteristics;

FIG. 5 is a flowchart showing a typical processing flow of the first embodiment;

FIGS. 6A through 6D are schematic views showing an example of how behavior characteristics are reflected in the attributes of characters;

FIG. 7 shows a table of typical attributes of characters;

FIG. 17 is a schematic view for explaining another variation.

DETAILED DESCRIPTION OF THE PREFERRED EMBODIMENTS

Some preferred embodiments of the present disclosure will now be described below in reference to the accompanying drawings. The description will be given under following headings.
<1. First embodiment>
<2. Second embodiment>
<3. Third embodiment>
<4. Fourth embodiment>
<5. Variations>

It should be noted that the embodiments and variations to be explained hereunder are preferred concrete examples of the present disclosure and are not limitative of the disclosure.

1. First Embodiment

[System Overview]

Figure 1:
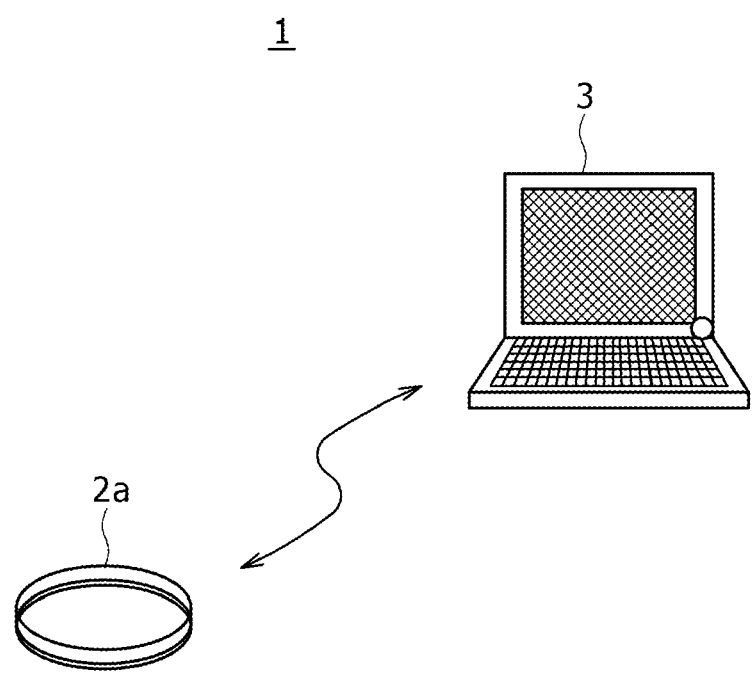
FIG. 1 is a schematic view outlining a typical system according to one embodiment of the present disclosure.

FIG. 1 shows a typical system according to this embodiment of the present disclosure. The system 1 in FIG. 1 includes a power generation device 2a and a host apparatus 3. The power generation device 2a and host apparatus 3 each have a communication function. The communication function allows the power generation device 2a and host apparatus 3 to communicate with each other in wired or wireless fashion. Alternatively, a USB (Universal Serial Bus) cable may be used to establish connection and permit communication between the power generation device 2a and the host apparatus 3.

The power generation device (also called the gadget) 2a may have approximately the same shape as an accessory, for example. In this example, the power generation device 2a has the shape of a ring. Alternatively, the power generation device 2a may have the shape of a wristband. It is preferred that the power generation device 2a be shaped to be exposed when worn by a user. When shaped in this manner, the power generation device 2a may be used by the user not as a portable measuring instrument but as part of his or her fashion. The shape of the power generation device 2a may be changed as appropriate and afforded good designability. The power generation device 2a has no need to be equipped with a battery, for example, so that the device can be shaped as desired.

The power generation device 2a has one or a plurality of power generation units. The power generation units generate power based on energies that exist in the environment. For example, the power generation units may generate electric power by tapping light, heat, vibration, and radio wave. These energies are not limited to the natural world. The heat may come from the user's body surface and the vibration from the user's movement, for example. The power generation device 2a acquires power generation information from the power generation units. Using its communication function, the power generation device 2a transmits the acquired power generation information to the host apparatus 3.

The host apparatus 3 may be a personal computer, for example. Alternatively, the host apparatus 3 may be a video game machine. As another alterative, the host apparatus 3 may be a portable electronic apparatus such as a mobile phone or a smartphone. The host apparatus 3 receives the power generation information from the power generation device 2a. Based on the power generation information thus received, the host apparatus 3 identifies the behavior characteristic of the user who uses the power generation device 2a. The user's behavior characteristic refers to a feature of the user's behavior and is a concept that includes the user's behavioral pattern as well as the user's tastes and preferences stemming from his or her behavioral trait.

[Structure of the Power Generation Device]

FIG. 2 shows a typical overall structure of the power generation device 2a. In FIG. 2, thick lines denote paths through which power is supplied and thin lines represent paths through which signals are transmitted. For example, the power generation device 2a may have four power generation units: a vibration power generation unit 11a that generates power in response to vibrations; a solar power generation unit 11b that generates power by tapping the sunlight; a temperature difference power generation unit 11c that generates power by drawing on the differences in temperature on the user's body surface; and a radio wave power generation unit 11d that generates power using radio waves. Where the individual power generation units need not be distinguished from one another, they may be generically referred to as the power generation units 11. The power generation units 11 may be structured in a commonly known manner. For example, the power generation units 11 may each operate on a different principle of power generation. Alternatively, they may operate on the same principle of power generation. For example, although operating on the same principle of solar power generation, one solar power generation unit may use a dye-sensitized solar cell and another solar power generation unit may utilize an amorphous silicon (Si) solar cell, the two units being set up separately.

The power generation units 11 are connected to a power control unit 20. The power control unit 20 measures the electric power and electric energy generated per unit time by each of the power generation units 11. The electric power and electric energies thus measured constitute typical power generation information. If a given power generation unit 11 generates AC (alternating current) power, the power control unit 20 rectifies the generated AC power. The power control unit 20 is connected with an MCU (micro controller unit) 12. The power control unit 20 supplies the MCU 12 with data relating to the power generation information (simply called the power generation information hereunder where appropriate).

The MCU 12 controls components of the power generation device 2a. For example, the MCU 12 may act as a rewrite unit that controls recording and reproduction of data to and from a memory 13 and as a control unit that controls communications with the host apparatus 3. The communication here may be Near Field Communication based on the Bluetooth (registered trademark) wireless technology standard, for example. Needless to say, communications may be carried out alternatively in accordance with other suitable standards. The MCU 12 transmits the power generation information fed from the power control unit 20 to the host apparatus 3 via an interface (I/F) 14.

The memory 13 is connected with the MCU 12. The memory 13 is a nonvolatile memory such as EEPROM (Electrically Erasable and Programmable Read Only Memory). The MCU 12 writes to the memory 13 the power generation information supplied from the power control unit 20. Alternatively, the MCU 12 may write to the memory 13 another user's power generation information acquired through communication so as to rewrite the power generation information already stored in the memory 13.

Incidentally, the MCU 12, memory 13, and interface 14 operate on a drive voltage generated by, say, the power from the power generation units 11. That is, the power from the power generation units 11 is supplied to the power control unit 20. From the power thus supplied, the power control unit 20 generates the drive voltage on which the MCU 12 operates. The drive voltage is fed from the power control unit 20 to the MCU 12 to drive the latter. Likewise, the power control unit 20 feeds power to the memory 13 and interface 14.

The interface 14 interfaces with the host apparatus 3. Communications with the host apparatus 3 are carried out through the interface 14. In an example of this embodiment of the disclosure, the host apparatus 3 may supply power to the power generation device 2a. The power generation device 2a is connected to the host apparatus 3 via, say, a USB cable so that data may be exchanged between the power generation device 2a and the host apparatus 3. When the power generation device 2a is connected to the host apparatus 3, the host apparatus 3 feeds power to the power control unit 20 of the power generation device 2a through a suitable line. Based on the power thus supplied, the power control unit 20 generates the drive voltage on which the MCU 12 and other components operate, and supplies the generated drive voltage to these components.

One method adapted to generate power generation information may involve preparing three parameters regarding power generation such as electric power and electric energy for use in combination with seven types of power generation units, which makes 21-digit data notation possible. If three kinds of data are extracted for each of the 21 digits using suitable parameters, three to the twenty-first power data combinations may be reproduced. If it is assumed that M stands for the type of generator, N for the number of parameters related to power generation and L for the number of data generated from the parameters, then one record length (M×L)×log 2N bits may be reproduced.

[Structure of the Power Control Unit]

FIG. 3 shows a typical structure of the power control unit 20. For purpose of simplification, the power generation units are represented by the vibration power generation unit 11a and solar power generation unit 11b in FIG. 3.

The vibration power generation unit 11a operates to generate an AC voltage. The generated AC voltage is supplied to the power control unit 20. A rectifier circuit 21 in the power control unit 20 converts the supplied AC voltage to a DC (direct current) voltage. The DC voltage resulting from the conversion is sent to a power generation measurement unit 22. When supplied with the DC voltage and the concomitant amount of current, the power generation measurement unit 22 measures the electric power and electric energy generated per unit time. The unit time may be one second, one minute, or some other suitable time increment.

The power generation measurement unit 22 is connected with a real-time clock (RTC) 27. Thus the power generation measurement unit 22 can measure the electric power and electric energy generated per unit time using time information fed from the RTC 27. The electric power and electric energy thus measured per unit time are supplied as typical power generation information to a power generation information management unit 26. The power generation information management unit 26 supplies the power generation information from the vibration power generation unit 11a to the MCU 12 (FIG. 2) via a signal line L1.

The solar power generation unit 11b operates to generate a DC voltage. The DC voltage thus generated is fed to the power control unit 20 and to a power generation measurement unit 24. In reference to the time information from the RTC 27 and based on the supplied DC voltage and amount of current, the power generation measurement unit 24 measures the electric power and electric energy generated per unit time. The electric power and electric energy thus measured per unit time are supplied as typical power generation information to the power generation information management unit 26. The power generation information management unit 26 supplies the power generation information from the solar power generation unit 11b to the MCU 12 via the signal line L1. The power generation information of the temperature difference power generation unit 11c and of the radio wave power generation unit 11d is measured in like manner. The power generation information thus measured is sent to the MCU 12 via the power generation information management unit 26.

Alternatively, the power generation information may be stored in the memory 13. For example, the power generation information may be measured at predetermined times of day. The measured power generation information may also be stored in increments of a week or a month.

The voltage from each of the power generation units is output through a backflow prevention diode. As explained above, the rectifier circuit 21 converts the AC voltage generated by the vibration power generation unit 11a into a DC voltage. The DC voltage derived from the conversion is output via a diode 23. The DC voltage generated by the solar power generation unit 11b is output via a diode 25. Of these output DC voltages, the highest voltage is supplied onto a power line L2, for example. The RTC 27 is connected to the power line L2. The voltage on which the RTC 27 operates is supplied from the power line L2 to the RTC 27.

An electricity storage device 28 is connected to the power line L2. The electricity storage device 28 may include an electric double layer capacitor, for example. The electricity storage device 28 is charged with the voltage supplied over the power line L2. A drive voltage derived from the voltage stored in the electricity storage device 28 causes the MCU 12 and memory 13 to operate, for example. A conversion unit, not shown, may be provided as appropriate on the output side of the electricity storage device 28 to convert the voltage on the power line L2 into a voltage corresponding to the MCU 12 and memory 13. Alternatively, the electricity storage device 28 may be supplied with a voltage from the host apparatus 3.

In the manner described above, the power generation information from the individual power generation units is sent from the power control unit 20 to the MCU 12. In turn, the MCU 12 feeds the power generation information to the host apparatus 3 through the interface 14. For example, the power generation information may be transmitted wirelessly to the host apparatus 3. Incidentally, the above-described structure of the power control unit 20 is merely an example. Alternatively, the power control unit 20 may include a CPU (central processing unit) or the like that controls the components of the power control unit 20.

The host apparatus 3 receives the power generation information sent from the power generation device 2a. In accordance with the received power generation information, the host apparatus 3 determines the behavior characteristic of the user of the power generation device 2a. For example, a CPU of the host apparatus 3 may carry out the process of determining the user's behavior characteristic. That is, the host apparatus 3 functions as a typical identification apparatus. Alternatively, the MCU 12 of the power generation device 2a may perform the process of determining the user's behavior characteristic. In this case, the power generation device 2a functions as a typical identification apparatus.

[Determination of the Behavior Characteristic]

A typical method adapted to determine the behavior characteristic in accordance with power generation information is outlined below in reference to FIGS. 4A to 4D. FIGS. 4A to 4D show four patterns of power generation information. The height of each bar in graphs schematically represents the amount of power generated by the corresponding power generation unit.

With regard to the power generation information shown in FIG. 4A, the largest amount of power is generated by the solar power generation unit 11b. This reveals that the user spends much time outdoors. Meanwhile, the amount of power generated by the radio wave power generation unit 11d is appreciably low. This indicates that the user is active in areas where radio waves are difficult to reach (e.g., in the mountains). The amount of power generated by the vibration power generation unit 11a and that generated by the temperature difference power generation unit 11c are approximately on the ordinary level. This means that the user's level of activity is approximately that of walking. With these pieces of power generation information taken into account, the pattern of the power generation information of FIG. 4A is identified with the behavior characteristic of "enjoys outdoor activities."

With regard to the power generation information shown in FIG. 4B, the amount of power generated by the vibration power generation unit 11a and that generated by the solar power generation unit 11b are high. Also, the amount of power generated by the temperature difference power generation unit 11c is high. The amount of power generated by the radio wave power generation unit 11d is approximately on the ordinary level. With this pattern of power generation information, it is determined that the user is being very active outdoors. That is, the behavior characteristic of "enjoys doing sports" is identified.

With regard to the power generation information shown in FIG. 4C, the amount of power generated by the vibration power generation unit 11a and that generated by the solar power generation unit 11b are significantly low. The amount of power generated by the temperature difference power generation unit 11c and that generated by the radio wave power generation unit 11d are a little lower than the ordinary level. With this pattern of power generation information, it is determined that the user tends to stay indoors and is not very active. That is, the behavior characteristic of "mostly stays indoors" is identified.

With regard to the power generation information shown in FIG. 4D, the amount of power generated by the vibration power generation unit 11a and that generated by the solar power generation unit 11b are approximately on the ordinary level. The fact that the amount of power generated by the temperature difference power generation unit 11c is a little high indicates that the user is somewhat active. The amount of power generated by the radio wave power generation unit 11d is appreciably high. That means the user is in locations where radio waves are easy to reach (e.g., in an urban area). With these pieces of information taken into account, the pattern of the power generation information of FIG. 4D is identified with the behavior characteristic of "often goes to town." The above-mentioned behavior characteristics may be each represented by a suitable bit (or byte) string. It may be determined that if values of bit strings representing two behavior characteristics coincide with each other, the two behavior characteristics are in fact the same. It may also be determined that the closer the bit string values are to each other, the more similar the corresponding behavior characteristics are to each other. Data representative of behavior characteristics may be simply referred to as behavior characteristics hereunder where appropriate.

In the manner described above, the behavior characteristic is identified in accordance with the amounts of power generated by different power generation units. The above-mentioned behavior characteristics are merely examples and may be changed as appropriate. There may be stored a table that associates relative ratios of the amounts of power generated by the individual power generation units with behavior characteristics corresponding to the ratios. Referencing that table will then identify the behavior characteristic of interest. If there is no such table stipulating ratios corresponding to the ratios of actual amounts of power generated, approximate ratios may be used instead. Furthermore, the table may be changed in keeping with such user information as users' ages, their places of residence and their genders.

[Processing Flow]

FIG. 5 shows a typical processing flow of the first embodiment. In FIG. 5, the left side shows the processing flow of the power generation device 2a and the right side shows the processing flow of the host apparatus 3.

In the process of step S1, at least one of the four power generation units applies energy to the power generation device 2a. For example, the solar power generation device 11b feeds a DC voltage to the power generation device 2a. The process then proceeds to step S2.

In step S2, it is determined whether the amount of electric charge in the electricity storage device 28 is sufficient to operate the MCU 12 and memory 13. For example, a threshold value is set, and the amount of stored electricity is determined to be sufficient if it exceeds the threshold value. The determination is performed by the power control unit 20. If the amount of electric charge is not sufficient, the process returns to step S1. If it is determined that the amount of electric charge is higher than the threshold value and thus sufficient, the process proceeds to step S3.

In step S3, the MCU 12, memory 13, etc., are connected as a load to the electricity storage device 28. In practice, switches are provided between the electricity storage device 28 and the elements such as the MCU 12. Turning on these switches connects those elements including the MCU 12 to the electricity storage device 28. The power control unit 20 controls ON/OFF of the switches. If stable power can be supplied to the MCU 12, the MCU 12 may be continuously turned on so that the MCU 12 monitors the amount of electric charge in the electricity storage device 28 and controls ON/OFF of the switches.

The voltage fed from the electricity storage device 28 activates the MCU 12. The MCU 12 determines whether the voltage it operates on comes from the power generation unit 11 or from the host apparatus 3. This determination is performed by the MCU 12, for example, by detecting whether or not the power generation device 2a is connected to the host apparatus 3. The detecting process of the MCU 12 may be accomplished by detecting the connection with mechanical means or by detecting the presence or absence of a particular signal input to the MCU 12.

If the power generation device 2a is connected to the host apparatus 3, the host apparatus 3 supplies a voltage to the electricity storage device 28 of the power generation device 2a. Thus the MCU 12 uses as its power source the power supplied from the host apparatus 3. In this case, the result of the determination in step S3 is negative (No), so that the process proceeds to step S7.

If the power generation device 2a is not connected to the host apparatus 3, the MCU 12 uses as its power source the power supplied from at least one of the power generation units. In this case, the result of the determination in step S3 is affirmative (Yes), so that the process proceeds to step S4.

In step S4, the amount of power generated by each of the power generation units is measured. For example, the power control unit 20 may measure the amounts of power generated by the vibration power generation unit 11a, solar power generation unit 11b, temperature difference power generation unit 11c, and radio wave power generation unit 11d. The measured amounts of power are sent from the power control unit 20 to the MCU 12 as the power generation information. The process then proceeds to step S5.

In step S5, the power generation information is stored into the memory 13 under control of the MCU 12. The process then proceeds to step S6. In step S6, the power generation device 2a is placed in a sleep state. For example, the switch between the MCU 12 and the electricity storage device 28 is turned off. The process then returns to step S1. Alternatively, the processing by the power generation device 2a may be carried out periodically. As another alternative, the processing may be repeated from step S1 upon elapse of a predetermined time period following the process of step S6.

When the result of the determination in step S3 is negative (No), the process proceeds to step S7. In step S7, processes of communication with the host apparatus 3 are carried out. For example, three processes are performed in step S7: a process of establishing communication with the host apparatus 3, a process of transmitting the power generation information stored in the memory 13, and a process of cutting off communication with the host apparatus 3.

The processing flow on the side of the host apparatus 3 is explained next. The processing by the host apparatus 3 is carried out in response to the process of step S7 performed by the power generation device 2a. Initially in step S8, the process of establishing connection with the power generation device 2a is performed. If the connection is not established, the host apparatus may display an error message or generate an alarm sound. When the connection with the power generation device 2a is established, the process proceeds to step S9.

In step S9, the host apparatus 3 acquires the power generation information by receiving it from the power generation device 2a. The acquired power generation information may be stored in a storage unit of the host apparatus 3. The process then proceeds to step S10. In step S10, the power generation information is analyzed. The process proceeds to step S11, in which the user's behavior characteristic is identified by analyzing the power generation information.

The data about the behavior characteristic determined by the host apparatus 3 may be transmitted to and received by the power generation device 2a. The received behavior characteristic may be stored into the memory 13. Further, the appearance of the power generation device 2a may be changed in accordance with the behavior characteristic. For example, a light emitting unit such as LED (light emitting diode) is attached to the power generation device 2a. If the above-mentioned behavior characteristic "enjoys outdoor activities" is transmitted from the host apparatus 3, the light emitting unit may glow in green. In the case of the above-mentioned behavior characteristic of "enjoys doing sports," the light emitting unit may glow in red. In the case of the above-mentioned behavior characteristic of "mostly stays indoors," the light emitting unit may glow in black. If the above-mentioned behavior characteristic of "often goes to town" is transmitted, the light emitting unit may glow in yellow. In such manner, the appearance of the power generation device 2a may vary according to the behavior characteristic.

As described above, the first embodiment of this disclosure can determine the behavior characteristic of the user of the power generation device in accordance with the power generation information obtained from the power generation units.

2. Second Embodiment

The second embodiment of the present disclosure is explained below. The second embodiment makes the user's behavior characteristic reflected in a virtual object. Specifically, a video game character (simply called character hereunder where appropriate) may be generated as a typical virtual object. The attributes of the character may be changed in keeping with the behavior characteristic. The power generation information may also be reflected in the character's attributes. The power generation device and the related units of the second embodiment have the same structures as those of the first embodiment, so that their explanations will be omitted hereunder where redundant.

[Behavior Characteristic Reflected in the Character]

A typical method for having the behavior characteristic reflected in the character is outlined below with reference to FIGS. 6A through 6D. The power generation information and behavior characteristics shown in FIGS. 6A through 6D are the same as those in FIGS. 4A through 4D. The process for having the behavior characteristic reflected in the character which will be discussed below may be performed by the host apparatus 3, for example. The process may instead be carried out by the power generation device 2a. Although images of the characters are explained by words in FIGS. 6A through 6D, the figures, designs, and other features of the characters may be set as desired. The characters are not limited to persons and may include animals and virtual creatures (e.g., monsters).

From the power generation information shown in FIG. 6A, the behavior characteristic of "enjoys outdoor activities" is identified. Having this behavior characteristic reflected in the character, there may be created a "character living in the mountains" which would evoke an image of outdoor activities. From the power generation information shown in FIG. 6B, the behavior characteristic of "enjoys doing sports" is identified. Having this behavior characteristic reflected in the character, there may be created a "sturdy warrior" which would evoke an image of a muscular body.

From the power generation information shown in FIG. 6C, the behavior characteristic of "mostly stays indoors" is identified. Having this behavior characteristic reflected in the character, there may be created a "witch dressed in black" which would evoke an image of a person with little social contact. From the power generation information shown in FIG. 6D, the behavior characteristic of "often goes to town" is identified. Having this behavior characteristic reflected in the character, there may be created a "mischievous dwarf" which would evoke an image of a person who loves to play.

The above example is one in which the character is created in accordance with the behavior characteristic. Alternatively, the attributes of the character may be changed in keeping with the behavior characteristic. For example, for each game character, there are defined such attributes as a "growth process" in which the character grows up battling or otherwise interacting with other characters in a virtual space, "status (also called level)," "occupation," "items," and "intelligence." These attributes may be combined with another. The attributes indicated here as examples may be changed in accordance with the behavior characteristic. For example, where the amount of power generated by the vibration power generation unit 11a is significantly high so that the behavior characteristic of "enjoys doing sports" is identified, the growth of the character in question may be promoted. Having the behavior characteristic reflected in a given character's attributes, that character can be differentiated from characters owned by other users. It may also be possible to encourage the user to start doing sports or otherwise change his or her behavior in order to let his or her character grow.

The power generation information itself may be reflected in the character's attributes. For example, the character may be given an attribute or may have its attributes changed in conjunction with the energy used by the power generation units. As the character's attributes, for example, there are defined water, fire, earth, wind, darkness, holiness, and void. An example of how an attribute is given to a character is explained below. If the amount of power generated by the vibration power generation unit 11a is high, the attribute of earth may be given; if the amount of power generation by the vibration power generation unit 11a is low, the attribute of wind may be given. If the amount of power generated by the solar power generation unit 11b is high, the attribute of holiness which is an angelic element may be given; if the amount of power generated by the solar power generation unit 11b is low, the attribute of darkness which is a demonic element may be given. If the amount of power generated by the temperature difference power generation unit 11c is high, the attribute of fire may be given; if the amount of power generated by the temperature difference power generation unit 11c is low, the attribute of water may be given. If the amounts of power generated by all power generation units are low (below certain reference values), the attribute is set to be absent. Alternatively, each of the power generation units 11 may represent one attribute.

Among the attributes, there exist correlations of advantages and disadvantages. For example, a character with the attribute of water is supposed to have an advantage over a character with the attribute of fire. The attributes may be combined as desired. For example, such correlations may be set that, whereas the character with the attribute of fire is at a disadvantage against the character with the attribute of water, a character having the attributes of both darkness and fire has an advantage over the character with the attribute of water.

As shown in FIG. 7, the characters may be set in accordance with such attributes as water, fire, holiness, and darkness. For example, for each character, a character ID and a character name for identifying the character are assigned. From the power generation information of the power generation units, the attributes such as water, fire, holiness and darkness are determined, and in turn, the character is determined according to the attributes. The table for determining a character such as the one shown in FIG. 7 may be updated as appropriate, for example, when a new character is added.

Explained below is a typical process for having power generation information reflected in a character's attributes. The process discussed below is carried out using software. In the description that follows, the power generation units are assumed to be made up of a solar power generation unit that uses an amorphous silicon (Si) solar cell (identified with reference character 11e hereunder where appropriate), and another solar power generation unit that utilizes a dye-sensitized solar cell (identified with reference character 11f hereunder where appropriate).

The amorphous silicon solar cell has the property of generating a large amount of power when the intensity of illumination is higher than a predetermined level, and generating a low amount of power when the intensity of illumination is lower than the predetermined level. This means that when the user of the power generation device 2a spends much time outdoors, the amount of power generated by the amorphous silicon solar cell becomes high. This is because outdoor activities are usually done when the weather is fine, that is, when the intensity of illumination is high. Utilizing this property of the amorphous silicon solar cell, it can be determined whether or not the user spends much time outdoors.

On the other hand, the dye-sensitized solar cell generates a relatively low amount of power but generates power even when the intensity of illumination is low. The dye-sensitized solar cell can generate power under the illumination of lights such as a fluorescent lamp. Utilizing this property of the dye-sensitized solar cell, it can be determined whether or not the user spends time indoors.

Figure 8:
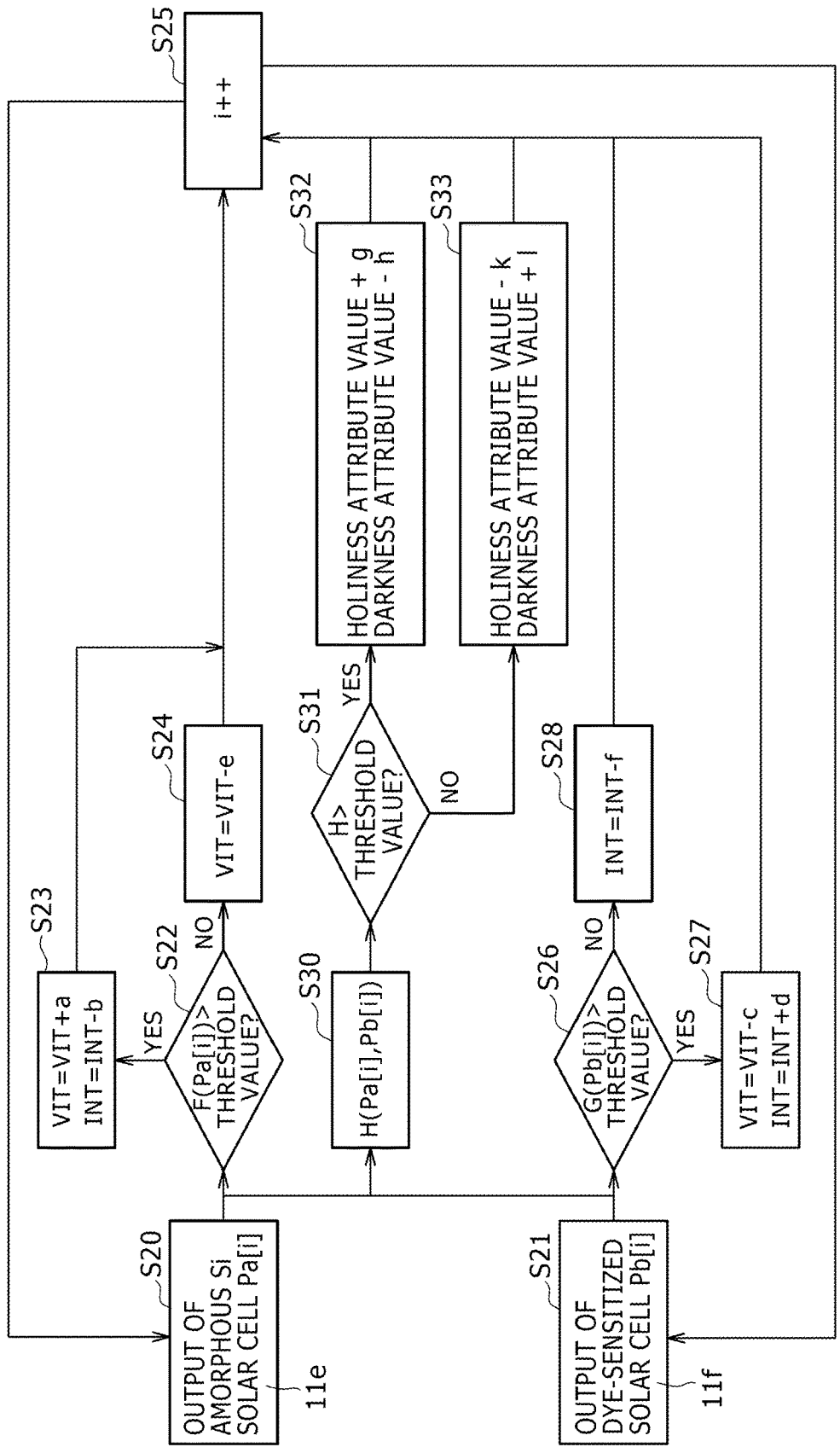
FIG. 8 is a flowchart showing a typical processing flow in which power generation information is reflected in the attributes of characters.

Specific details of the process will now be explained referring to FIG. 8. First, in steps S20 and S21, the power and voltage generated at a sampling time is are acquired. It is assumed here that Pa[i] and Pb[i] denote arrays of i-th data obtained at each sampling time as the outputs of the solar power generation unit 11e and the solar power generation unit 11f, respectively. Pa and Pb may be the arrays (output vectors) of Pa[i]=(power pa[i], voltage va[i], t[i]) and Pb[i] =(power pb[i], voltage vb[i], t[i]), respectively. The feature values of a character are calculated based on these output vectors. Since various evaluation functions can be used as the arithmetic expressions for this calculation, the functions used here are represented by F, G and H. The evaluation functions F and G are each provided for one output circuit. The evaluation function H takes a plurality of output circuits as its input. The evaluation functions F and G may be either different functions or the same function.

In step S22, a comparison is made between the function F(Pa[i]) and a threshold value. If it is determined that the function F(Pa[i]) is larger than the threshold value, the process proceeds to step S23. In step S23, a parameter "a" is added to a variable VIT representative of vitality. (The style of expressing this algorithm, such as VIT=VIT+a in step S23, conforms to that of C language.) In addition, in step S23, a parameter "b" is subtracted from a variable INT denoting intelligence. That is, from the fact that the function F(Pa[i]) indicative of the amount of power generated by the solar power generation unit 11e is larger than the threshold value, it is determined that the user spends time outdoors. Accordingly, the variable representing vitality is raised and the variable representing intelligence is lowered. The process then proceeds to step S25. In step S25, the variable "i" is incremented, and the process returns to step S20.

If the function F(Pa[i]) is equal to or smaller than the threshold value, the process proceeds to step S24. In step S24, a parameter "c" is subtracted from the variable VIT. That is, from the fact that the function F(Pa[i]) is smaller than the threshold value, it is determined that the user spends time indoors. Accordingly, the variable representing vitality is lowered. There are various kinds of indoor activities. The process is here intentionally rendered complicated by not uniquely processing the determination results of the discriminants, so that there is a part that the user cannot infer the cause and effect involved. This is intended to prevent the user from getting accustomed and losing interest. The variable INT is kept unchanged. The process then proceeds to step S25. In step S25, the variable "i" is incremented, and the process returns to step S20.

A similar process is performed with the function G(Pb[i]). In step S26, a comparison is made between the function G(Pb[i]) and a threshold value. The threshold value with which the function F(Pa[i]) is compared may be either the same as or different from the threshold value with which the function G(Pb[i]) is compared. If it is determined that the function G(Pb[i]) is larger than the threshold value, the process proceeds to step S27. In step S27, a parameter "c" is subtracted from the variable VIT representing vitality, and a parameter "d" is added to the variable INT denoting intelligence. The process then proceeds to step S25. In step S25, the variable "i" is incremented, and the process returns to step S21.

If it is determined that the function G(Pb[i]) is equal to or smaller than the threshold value, the process proceeds to step S28. In step S28, a parameter "f" is subtracted from the variable INT representing intelligence. The process then proceeds to step S25. In step S25, the variable "i" is incremented, and the process returns to step S21.

In step S30, a function H(Pa[i], Pb[i]) is calculated and in step S31 a comparison is made between the function H(Pa[i], Pb[i]) and a threshold value. This threshold value is set to be the same as or different from any of the other thresholds. Here, the function H is defined as H(Pa[i], Pb[i])=(output amount of power generated by the amorphous silicon solar cell at given points in time ts[i−1] and ts[i])+(output amount of power generated by the dye-sensitized solar cell at given points in time ts[i−1] and ts[i]).

If it is determined that the function H(Pa[i], Pb[i]) is larger than the threshold value, the process proceeds to step S32. In step S32, parameters "g" and "h" are used to increase the attribute value of holiness and decrease the attribute value of darkness. That is, the parameter "g" is added to the attribute value of holiness and the parameter "h" is subtracted from the attribute value of darkness. The process then proceeds to step S25. In step S25, the variable "i" is incremented, and the process returns to steps S20 and S21.

If it is determined that the function H(Pa[i], Pb[i]) is smaller than the threshold value, the process proceeds to step S33. In step S33, parameters "k" and "l" are used to decrease the attribute value of holiness and increase the attribute value of darkness. That is, the parameter "k" is subtracted from the attribute value of holiness and the parameter "l" is added to the attribute value of darkness. The process then proceeds to step s25. In step S25, the variable "i" is incremented, and the process returns to steps S20 and S21.

In steps S32 and S33, the tendency to the attribute of holiness becomes stronger the longer the user spends time in a bright place, and the tendency to the attribute of darkness becomes stronger the longer the user spends time in a dark place. This makes it possible to characterize virtual characters according to the surrounding environment of the user.

Figure 9:
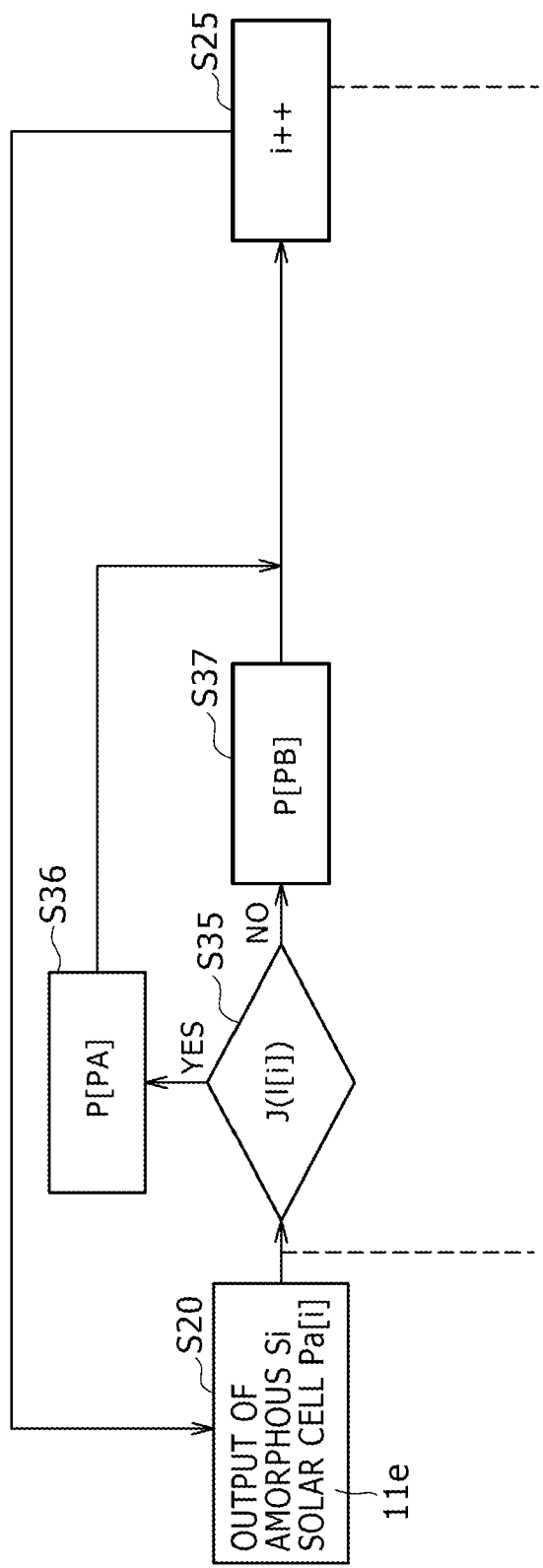
FIG. 9 is a flowchart showing another typical processing flow in which power generation information is reflected in the attributes of characters.

The processes in steps S22, S26 and S31 are not limited to the comparison with a threshold value. Alternatively, the attribute value may be changed when the function meets a specific condition. Although discriminants that determine whether or not an argument is larger than a threshold value are used here for the functions F, G and H, the threshold value and the discriminant may also be expressed by functions I and J. Further, while simple additions and subtractions using parameters were described above as the procedures for changing the feature quantities, they may also be executed using functions PA, PB, PC, PD and PE. Furthermore, these parameters may as well be processed by functions P[PA], P[PB], P[PC], P[PD] and P[PE] using PA, PB, PC, PD and PE as an argument. For example, as shown in FIG. 9, the routine may be configured such that if J(I[i])=TRUE in step S35, the process P[PA] is performed (in step S36), and if J(I[i])=FALSE, the process P[PB] is carried out (step S37). In such manner, the process for having power generation information reflected in a character's attributes is carried out, for example, by the host apparatus 3. In that case, the control unit of the host apparatus 3 functions as an attribute processing unit. Alternatively, the MCU 12 may perform this process.

[Processing Flow]

Figure 10:
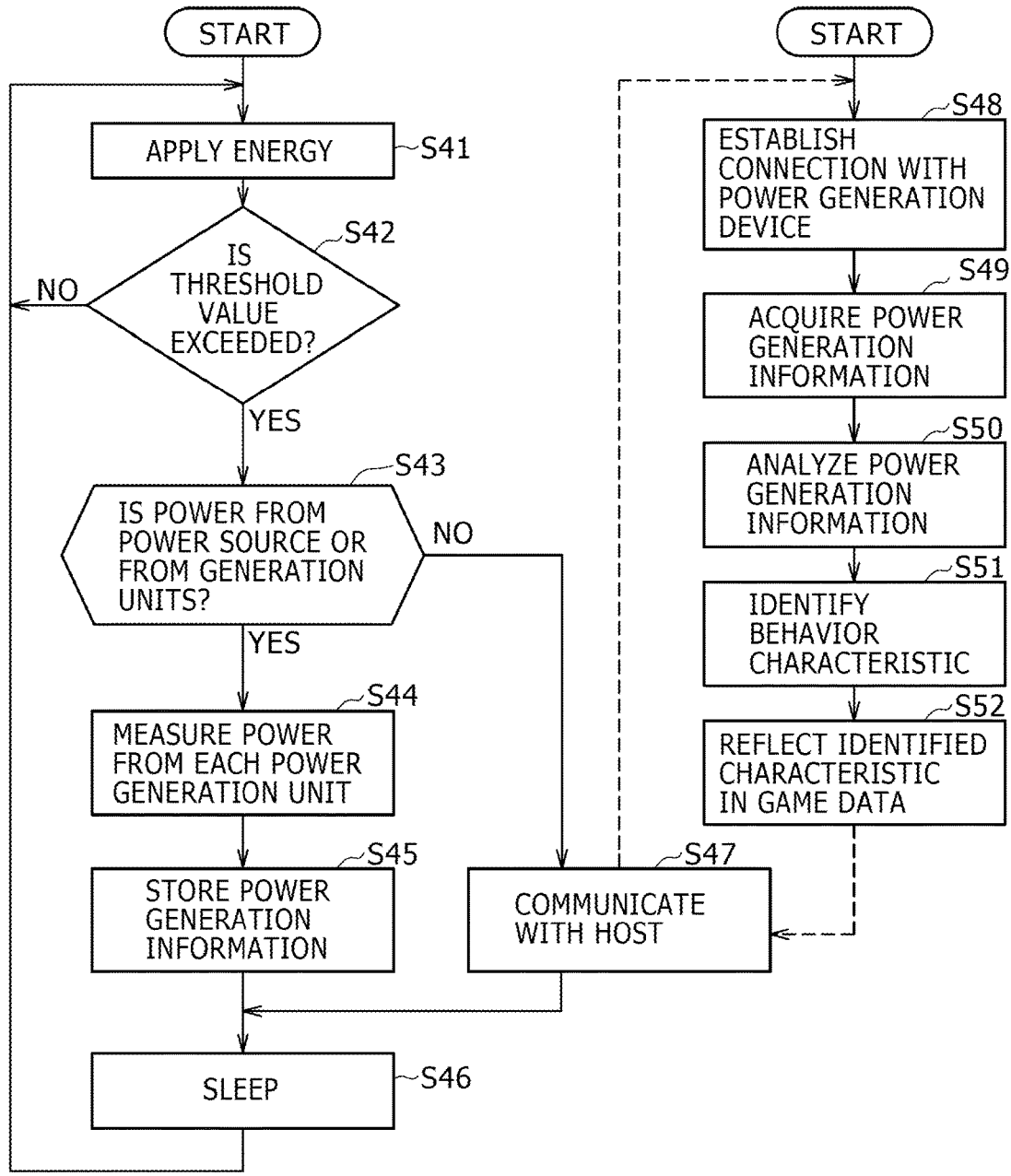
FIG. 10 is a flowchart showing a typical processing flow of a second embodiment of this disclosure.

FIG. 10 is a flowchart showing a typical processing flow of the second embodiment. Because the processing performed by the power generation device of the second embodiment (i.e., steps S41 through S46) is the same as that carried out by the power generation device of the first embodiment (i.e., step S1 through S6), the corresponding explanations will be omitted hereunder where redundant. In step S47, the power generation device 2a transmits the power generation information to the host apparatus 3 after establishing connection with it.

In step S48, the host apparatus 3 establishes the connection with the power generation device 2a. The process then proceeds to step S49. In step S49, the power generation information sent from the power generation device 2a is received by the host apparatus 3. The process then proceeds to step S50. In steps S50 and S51, the host apparatus 3 analyzes the received power generation information and identifies the behavior characteristic corresponding to the analyzed information. The process then proceeds to step S52. In step S52, the host apparatus 3 causes the behavior characteristic to be reflected in the game data. For example, the host apparatus 3 may create a virtual character reflecting the identified behavior characteristic.

Incidentally, the character created or otherwise processed in step S52 may be transmitted to another device (e.g., to a portable video game machine). The character may be uploaded to a server and disclosed to other users. The identifier (ID) for identifying the character may also be transmitted to the power generation device so that the appearance of the power generation device changes according to the identifier.

3. Third Embodiment

The third embodiment of the present disclosure is explained next. The power generation device for use in the third embodiment has a tag-like form that can be attached to the user's bag or clothes, and is provided with a display unit. The virtual character reflecting the user's behavior characteristic can be displayed on this display unit.

Figure 11:
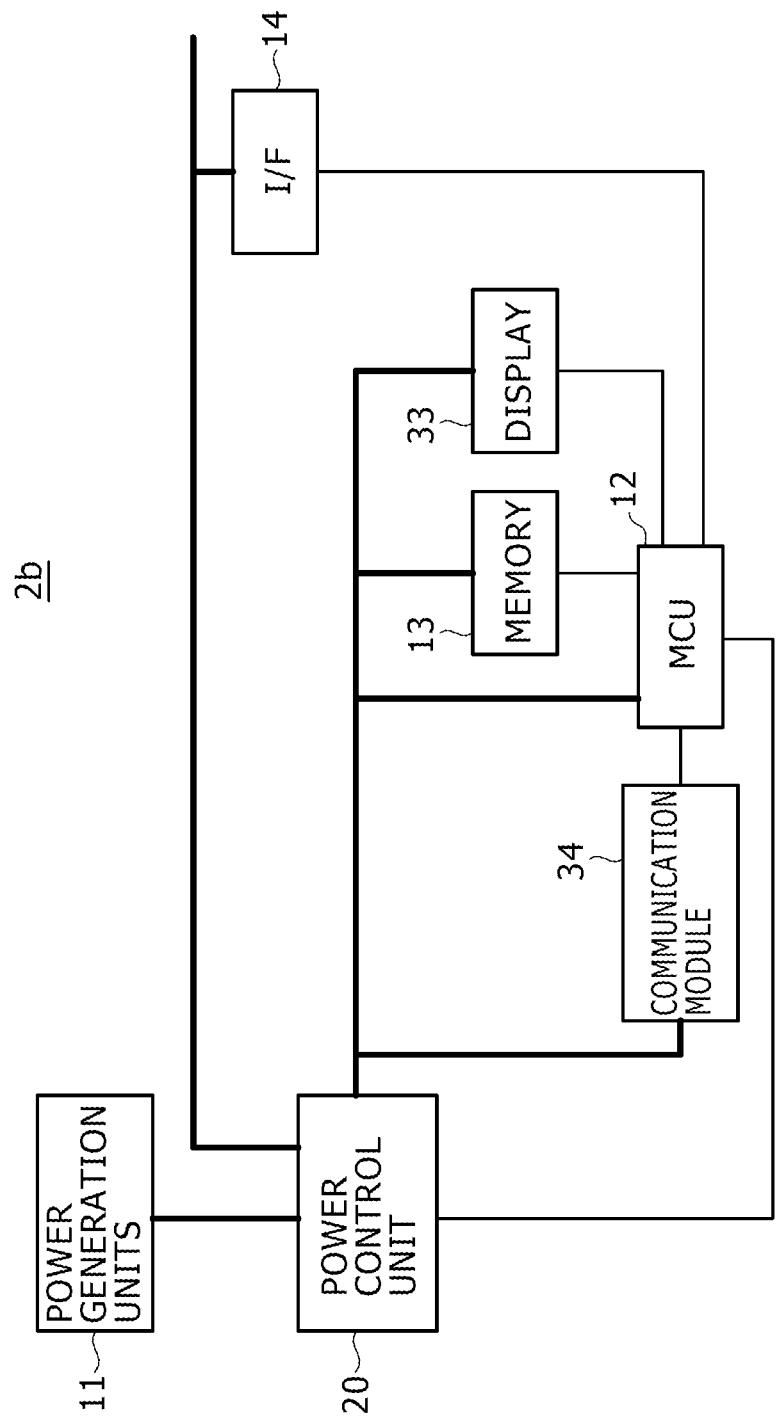
FIG. 11 is a block diagram showing a typical structure of a power generation device in a third embodiment of this disclosure.

FIG. 11 shows a typical structure of a power generation device 2b in the third embodiment. The power generation device 2b includes the power generation units 11, the power control unit 20, the MCU 12, the memory 13, and the interface 14. Although not shown, the power generation units 11 may include the vibration power generation unit 11a, the solar power generation unit 11b, etc., for example. The structures of these units and their functions are approximately the same as those of the power generation device 2a, so that their explanations will be omitted hereunder where redundant.

The power generation device 2b further includes a display unit 33 and a communication (RF (radio frequency)) module 34. The MCU 12 controls the display unit 33 and communication module 34. The display unit 33 may be an LCD (liquid crystal display) for example. Alternatively, the display unit 33 may be an organic EL (electroluminescence) display or some other type of display. The display unit 33 displays a video game character that reflects the user's behavior characteristic. Obviously, other information may also be displayed on the display unit 33. The character may be displayed continuously on the display unit 33 when the unit is supplied with power. Alternatively, the display of the character may be turned on or off in accordance with the user's operations.

The details of the process of getting the behavior characteristic reflected in the character are the same as those explained above in connection with the second embodiment, so that their explanations will be omitted hereunder where redundant. The process of having the behavior characteristic reflected in the character may be carried out by the MCU 12 or by the host apparatus 3.

The communication module 34 is connected to the MCU 12. The communication module 34 comes under control of the MCU 12. That is, the MCU 12 and communication module 34 function as a communication unit. The communication module 34 is a module that communicates with a power generation device owned by another user. Incidentally, the interface 14 and communication module 34 communicating with the host apparatus 3 may be integrated into a single structure. For purpose of explanation, the power generation device owned by another user is called a power generation device 2b' hereunder. The structure of the power generation device 2b' is appropriately the same as that of the power generation device 2b.

Specifically, whenever the power generation device 2b and another user's power generation device 2b' pass each other, their communication modules 34 communicate with each other. The communication may be performed in compliance with diverse communication standards (such as the Bluetooth wireless technology standard and the Zigbee (registered trademark) communication protocol). Below is an overall explanation of the communication carried out by the communication modules 34 upon passing with each other.

The communication module 34 keeps monitoring whether there is the power generation device 2b' within a predetermined distance (e.g., within several meters). If it is determined that the power generation device 2b' is present within the predetermined distance, communications take place between the communication module 34 of this power generation device 2b and that of the power generation device 2b', with the power generation information exchanged therebetween. For example, the power generation information read from the memory 13 by the MCU 12 is supplied to the communication module 34 and forwarded therefrom to the power generation device 2b'. A known communication method other than those cited above may be utilized instead. As another alternative, the user may be allowed to determine whether or not to transmit and receive power generation information.

The communication module 34 receives the power generation information from the power generation device 2b'. The received power generation information from the power generation device 2b' is supplied to the MCU 12. The MCU 12 writes the supplied power generation information from the power generation device 2b' to the memory 13. For example, the MCU 12 may replace the power generation information from the power generation units 11 stored in the memory 13 with the power generation information acquired by communication from the power generation device 2b'.

[Processing Flow]

Figure 12:
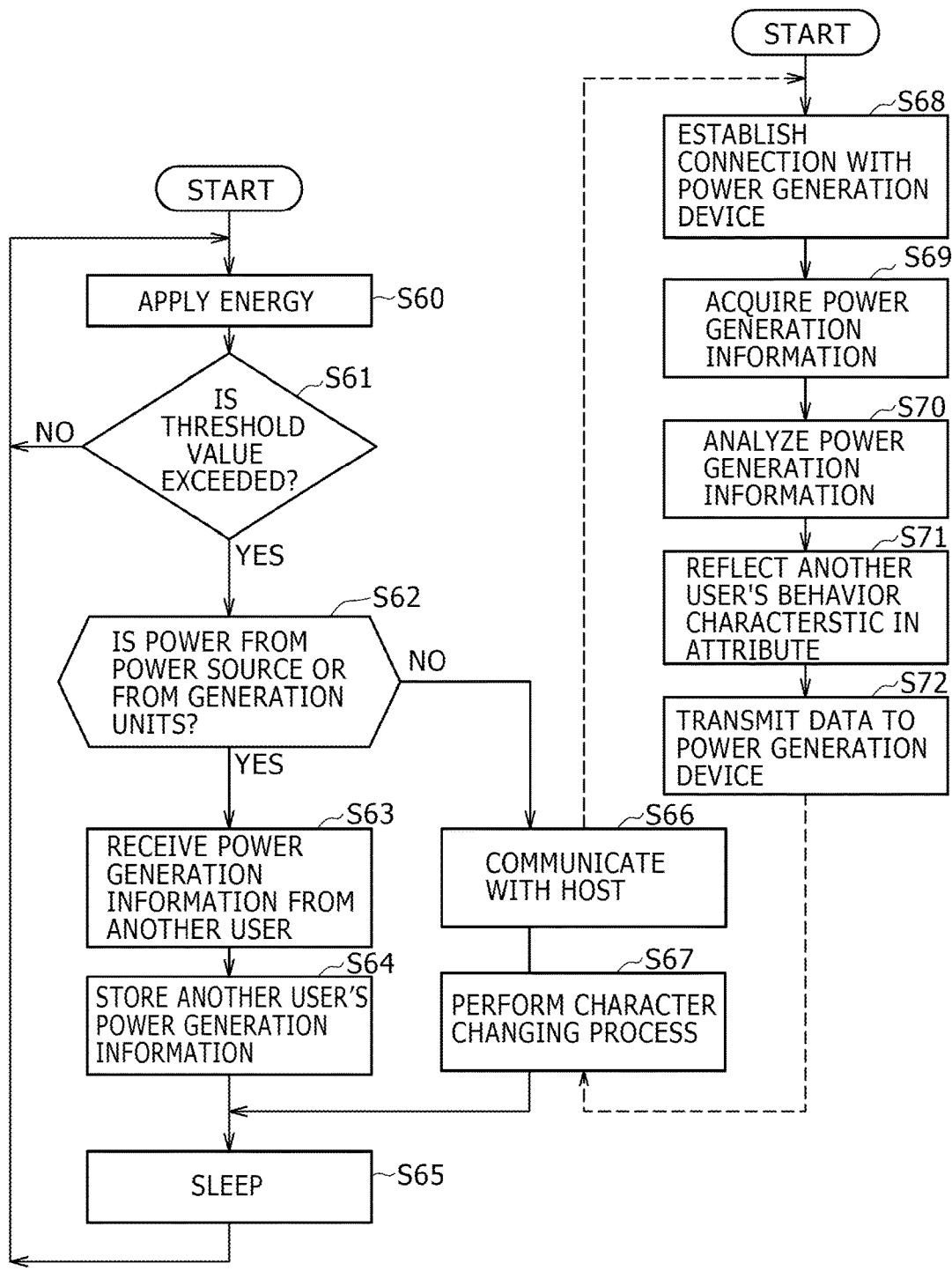
FIG. 12 is a flowchart showing a typical processing flow of the third embodiment.

FIG. 12 is a flowchart showing a typical processing flow of the third embodiment. It is assumed that before the process in FIG. 12 takes place, the power generation information from the power generation device 2b is measured and stored into the memory 13. It is also assumed that the user's behavior characteristic is identified from the power generation information and that a character reflecting the identified behavior characteristic is established. The character thus established may be displayed on the display unit 33.

In step S60, the power generation device 2b is energized. In step S61, it is determined whether the electric charging element 28 is charged with a sufficient voltage to operate the MCU 12, memory 13, interface 14, display unit 33, communication module 34 and the like. If it is determined that the amount of electric charge in the electric charging element 28 is not sufficient, control is returned to step S60. If it is determined that a sufficient amount of electric charge is in the electric charging element 28, control is passed to step S62. In step S62, it is determined whether the power is sourced from the power generation units or from the outside. As in step S3, it is determined here whether the power generation device 2b is connected to the host apparatus 3. If it is determined that the power is sourced from the power generation units, control is passed to step S63.

In step S63, the communication module 34 communicates with another module upon passing with each other. That is, the communication module 34 determines whether another power generation device 2b' is present within a predetermined range of the power generation device 2b. Although not shown, if another power generation device 2b' is not present within the predetermined range, control is passed to step S65. The power generation device 2b is then placed in a sleep state.

If it is determined that another power generation device 2b' is present within the predetermined range of the power generation device 2b, the communication module 34 receives power generation information from the power generation device 2b' upon passing each other. Control is then passed to step S64.

In step S64, the received power generation information is forwarded from the communication module 34 to the MCU 12. The MCU 12 stores the power generation information thus supplied into the memory 13. For example, the power generation information previously measured by the power generation device 2b and stored in the memory 13 may be replaced with the power generation information measured by the power generation device 2b'. Control is then passed to step S65 and the power generation device 2b is placed in the sleep state. The process of getting the power generation information rewritten is carried out when this user and the other user who owns the power generation device 2b' pass each other. The user remains unaware of this process taking place.

If it is determined in step S62 that the power is sourced from the host apparatus 3, control is passed to step S66. In step S66, the communication is established with the host apparatus 3. Also, the power generation information from the power generation device 2b' stored in the memory 13 is transmitted to the host apparatus 3. Step S66 is followed by step S67 in which a character changing process, to be discussed later, is carried out.

The processing on the side of the host apparatus 3 is explained below. In step S68, the connection with the power generation device 2b is established. Once the connection is established with the power generation device 2b, control is passed to step S69. In step S69, the power generation information sent from the power generation device 2b is received. Control is then passed to step S70.

In step S70, the power generation information is analyzed and the behavior characteristic is identified. Here, the power generation information received in step S69 comes from the power generation device 2b' owned by the other user. That is, in step S70, the behavior characteristic of the other user who owns the power generation device 2b' is identified. Control is then passed to step S71. In step S71, the other user's behavior characteristic identified in step S70 is reflected in the attribute of the character. For example, a virtual character reflecting the other user's behavior characteristic may be created. Control is then passed to step S72. In step S72, the display data of the character created in step S71 is transmitted from the host apparatus 3 to the power generation device 2b. The transmitted display data of the character is received by the communication module 34 and forwarded therefrom to the MCU 12.

In response to the process of step S72 performed by the host apparatus 3, the power generation device 2b carries out the character changing process (in step S67). The MCU 12 controls the display unit 33 to display the character based on the character display data sent from the host apparatus 3. The character display data from the host apparatus 3 may be stored into the memory 13, and the character may be displayed on the display 33 in response to the user's operations. Control is then passed to step S65 and the power generation device 2b is placed in the sleep state. The display of the character may be arranged to continue in the sleep state.

From the history of his or her behavior, the user possesses a certain image of the character. For example, after a vigorous physical exercise, the user may expect the character to have grown or have gained more items. With such an image in mind, the user verifies the character being displayed on the display unit 33. Then the character actually displayed on the display unit 33 may turn out to be one which reflects the other user's behavior characteristic and may be different from what the user has in mind. This discrepancy between the character imaged by the user and the actually displayed character may afford a heightened sense of surprise and thereby entertain the user. If the user likes the character reflecting the other user's behavior characteristic, that character may be stored into the memory 13.

Alternatively, the user's power generation information stored in the memory 13 need not be rewritten. This makes it possible to identify the user's behavior characteristic based on the power generation information coming from the power generation device 2b, and to have the behavior characteristic reflected in the attributes of the character. That is, the character based on the other user's behavior characteristic may be replaced again with the character based on this user's behavior characteristic.

It is also possible to create a new behavior characteristic by mixing the user's behavior characteristic with that of the other user. For example, if the user's behavior characteristic is "very often goes to town" and the other user's behavior characteristic is "moderately goes to town," a behavior characteristic of "relatively often goes to town" may be created. Specifically, the behavior characteristic data of two or more users may be averaged, and a new behavior characteristic corresponding to the mean value may be created. As another alternative, the generated behavior characteristic may be reflected in the character's attributes.

4. Fourth Embodiment

The fourth embodiment of the present disclosure is explained next. The fourth embodiment has a power generation device equipped with a sensor. The user's behavior characteristic is identified using information obtained from the attached sensor in addition to the power generation information. Also, when the user and another user who have similar behavior characteristics pass each other, the user is notified of the passing. Any suitable means may be adopted for notifying the user of the passing. Although the notification is made using display means in the fourth embodiment as one example, sound or vibration may instead be used. It is also possible to use those means in combination to make the notification.

Figure 13:
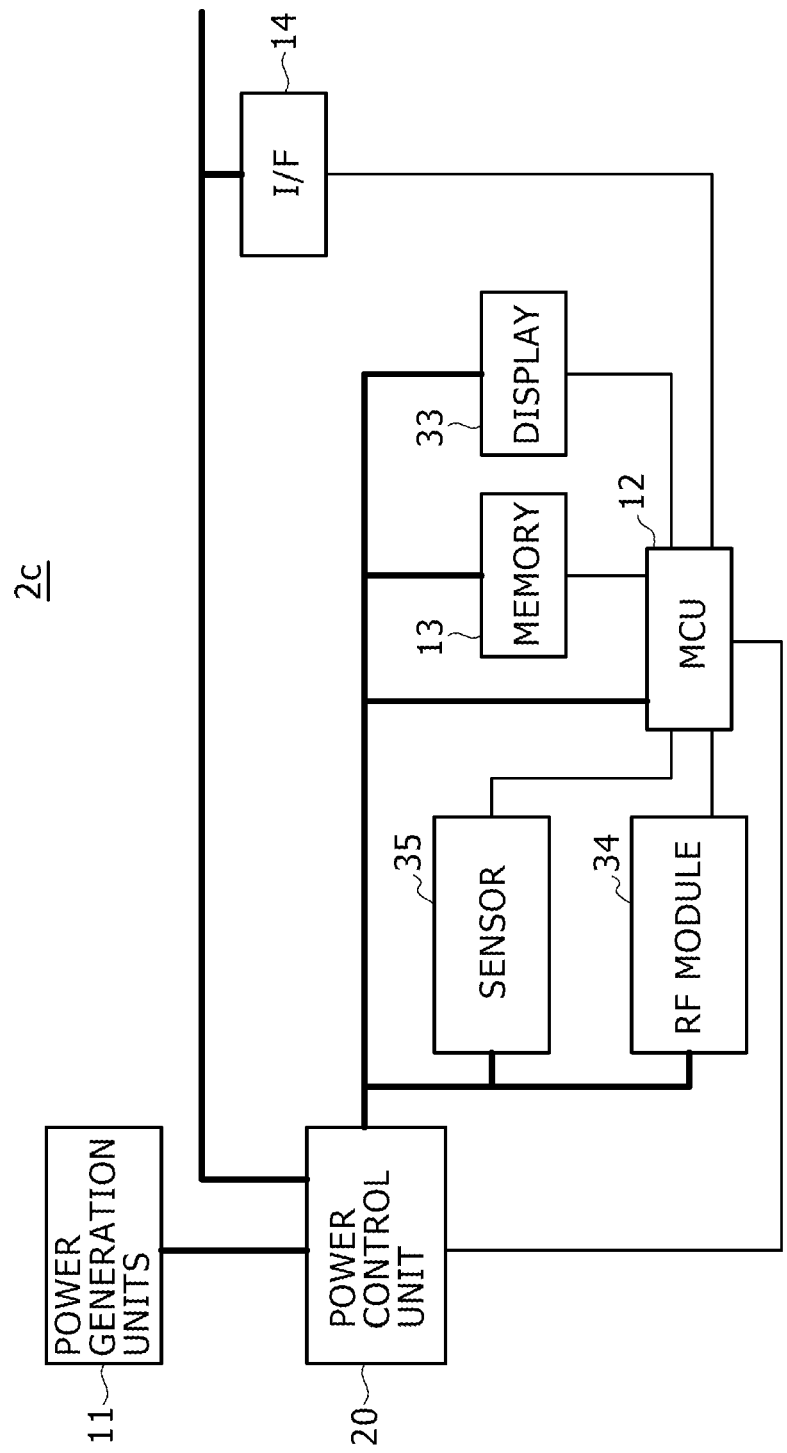
FIG. 13 is a block diagram showing a typical structure of a power generation device in a fourth embodiment of this disclosure.

FIG. 13 shows a typical configuration of a power generation device 2c in the fourth embodiment. The power generation device 2c has generally the same configuration as the power generation device 2b. That is, the power generation device 2c includes power generation units 11 such as a vibration power generation unit 11a and a solar power generation unit 11b, a power control unit 20, an MCU 12, a memory 13, an interface 14, a display unit 33, and a communication module 34. The details of the configuration are generally the same as those of the power generation device 2b. Therefore, their explanations will be omitted hereunder where redundant.

The power generation device 2c further includes a sensor 35. A variety of kinds of sensors may be employed as the sensor 35. For example, the sensor 35 may be a sensor acquiring position information such as latitude, longitude and altitude; acceleration sensor; gyro sensor; sensor acquiring meteorological conditions such as temperature or humidity; odor sensor; luminosity sensor; sound pressure sensor; or sensor detecting a specific substance. The sensor information acquired by the sensor 35 is supplied to the MCU 12.

The MCU 12 forwards the acquired sensor information and the power generation information fed from the power control unit 20 to the host apparatus 3. Given the sensor information and power generation information, the host apparatus 3 identifies the user's behavior characteristic. The concomitant use of the sensor information allows the user's behavior characteristic to be identified more specifically. For example, suppose that a GPS (Global Positioning System) device is used as a sensor 35 to detect position information. Using the information obtained by the GPS helps identify more precisely the location where the user is at. Thus the behavior characteristic of "enjoys outdoor activities" may be more specifically specified as "often goes to mountain-climbing" or "often hikes in the park," for example.

[Processing Flow]

Figure 14:
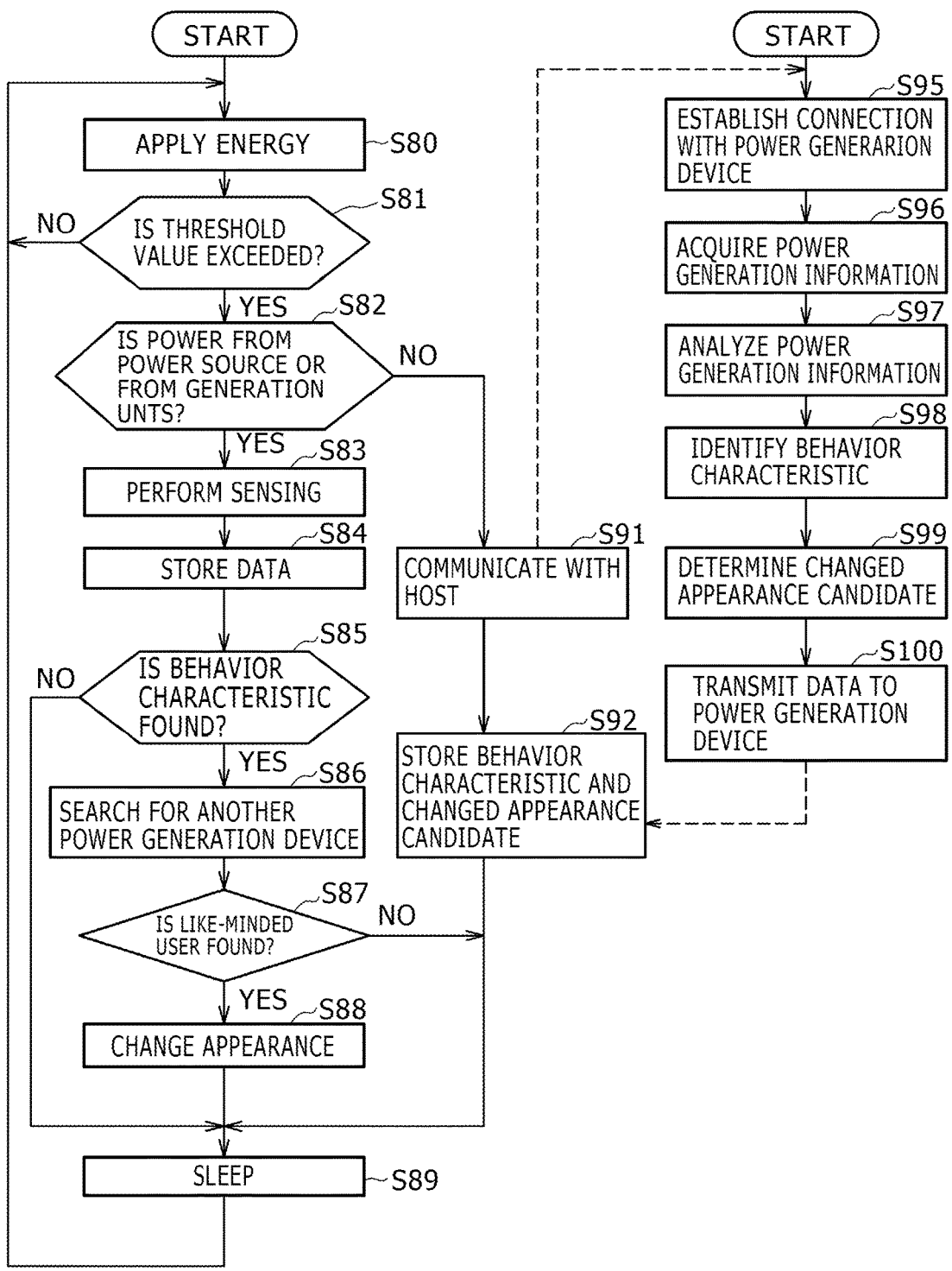
FIG. 14 is a flowchart showing a typical processing flow of the fourth embodiment.

FIG. 14 is a flowchart showing a typical processing flow of the fourth embodiment. In step S80, the power generation device 2c is energized. In step S81, it is determined whether the electricity storage device 28 is charged with a sufficient voltage to operate the MCU 12, memory 13, interface 14, display unit 33, and communication module 34. If it is determined that the amount of electric charge in the electricity storage device 28 is insufficient, the process returns to step S80. If it is determined that a sufficient amount of electric charge is in the electricity storage device 28, the process proceeds to step S82. In step S82, it is determined whether the power is sourced from the power generation units or from the outside. As in step S3, it is determined here whether the power generation device 2c is connected to the host apparatus 3. If it is determined that the power is sourced from the power generation units, the process proceeds to step S83.

In step S83, the sensor 35 operates to perform a sensing process. Also in step S83, the amounts of power generated by the power generation units are measured and the power generation information is obtained. The process then proceeds to step S84. In step S84, the power generation information and sensor information acquired in step S83 are stored into the memory 13. The process then proceeds to step S85.

In step S85, it is determined whether a behavior characteristic is stored in the memory 13. In this example, the host apparatus 3 identifies the behavior characteristic. Thus if the power generation device 2c has never been connected to the host apparatus 3, the behavior characteristic is not found in the memory 13. If no behavior characteristic is stored in the memory 13, the process proceeds to step S89 and the power generation device 2c is placed in the sleep state. If it is determined that the user's behavior characteristic is stored in the memory 13, the process proceeds to step S86.

In step S86, the process of searching for another power generation device (hereafter called a power generation device 2c' where appropriate) is carried out. This process may be performed by the communication module 34, for example. The communication module 34 performs searching to determine whether there exists a power generation device 2c' within a predetermined range (e.g., several meters) from where the power generation device 2c is located. For example, the communication module 34 may send out search messages to its surroundings and check for a response to the messages to see if a power generation device 2c' is present nearby. Step S86 may be carried out periodically, for example, at an interval of few seconds.

If it is determined in step S86 that a power generation device 2c' is present, the power generation devices 2c and 2c' communicate with each other. Through this communication, the two users' behavior characteristics are exchanged. The communication module 34 of the power generation device 2c receives the behavior characteristic sent from the power generation device 2c' and supplies the received behavior characteristic to the MCU 12. The process then proceeds to step S87.

The MCU 12 compares the behavior characteristic fed from the communication module 34 with that stored in the memory 13. For example, the MCU 12 may calculate the difference of data values between the two behavior characteristics. If the difference turns out to be equal to or smaller than a predetermined threshold value, the MCU 12 determines that the compared behavior characteristics are similar to each other. If the two behavior characteristics are thus determined to be similar, the MCU 12 may regard the user of the power generation device 2c' as a user that is like-minded with or sympathetic to the user of the power generation device 2c. If such user is not found after the user's behavior characteristic is compared with the behavior characteristic or characteristics of one or a plurality of users of power generation device or devices 2c', the process proceeds to step S89, and the power generation device 2c is placed in the sleep state.

If it is determined in step S87 that a like-minded user is present within the predetermined range, the process proceeds to step S88. In step S88, the processing of changing the appearance of the power generation device 2c is carried out using a predetermined suitable method. For example, the display unit 33 may be arranged to blink in a predetermined color. This process allows the user to recognize the nearby presence of another user who has a similar behavior characteristic. Steps S86 through S88 may be carried out when the user passes by another user. Upon recognizing that another user who just passed by has a behavior characteristic similar to his or hers, the user may feel a sense of affinity to the other user. The process then passes to step S89 and the power generation device 2c is placed in the sleep state.

If it is determined in step S82 that the power is sourced from the host apparatus 3, that is, the power generation device 2c is coupled with the host apparatus 3, the process proceeds to step S91. In step S91, the connection with the host apparatus 3 is established using the interface 14, for example. Once the connection with the host apparatus 3 is established, the power generation information and sensor information are transmitted to the host apparatus 3. Step S91 is followed by step S92, of which the details will be discussed later.

The process carried out by the host apparatus 3 is explained below. In step S95, the connection with the power generation device 2c is established. Once the connection is established, the process proceeds to step S96. In step S96, the power generation information and sensor information sent from the power generation device 2c are received. The process then proceeds to step S97. In step S97, the power generation information and sensor information are analyzed. The process then proceeds to step S98. In step S98, the user's behavior characteristic is identified from the power generation information and sensor information. The process then proceeds to step S99.

In step S99, a changed appearance candidate is determined which, if a like-minded user is found nearby, specifies how the appearance of the power generation device 2c will be changed. For example, a plurality of changed appearance candidates are presented to the user and one of them may be selected in response to the user's operation. Naturally, the host apparatus 3 may automatically set the changed appearance candidates. The power generation device 2c, not the host apparatus 3, may set the changed appearance candidates. The process then proceeds to step S100. In step S100, the data specifying the behavior characteristic as well as the changed appearance candidate is transmitted to the power generation device 2c.

In response to the process of step S100, step S92 is performed by the power generation device 2c. In step S92, the behavior characteristic and changed appearance candidate sent from the host apparatus 3 are stored into the memory 13. The process then proceeds to step S89 and the power generation device 2c is placed in the sleep state. Based on the behavior characteristic and changed appearance candidate stored in step S92, the above-mentioned steps S87 and S88 are carried out.

In this manner, the determination can be made whether there is any other user nearby who has a behavior characteristic appreciably similar to that of the user. The user may feel affinity to another user having a similar behavior characteristic, and a sense of community may be developed. Incidentally, the manner of changing the appearance may be varied depending on the degree of similarity in behavior characteristic. For example, if the behavior characteristics are identical to each other, the display unit blinks in red; if the behavior characteristics are somewhat similar to each other, the display unit blinks in green; and if the behavior characteristics are slightly similar to each other, the display unit blinks in yellow. The host apparatus in the fourth embodiment may be configured to determine the behavior characteristic in accordance with the sensor information and power generation information. The same also holds for the power generation device.

5. Variations

Some preferred embodiments have been explained heretofore. Embodiments of the present disclosure are not limited to them, and various variations may be made. Some of the variations are explained below.

[First Variation]

Figure 15:
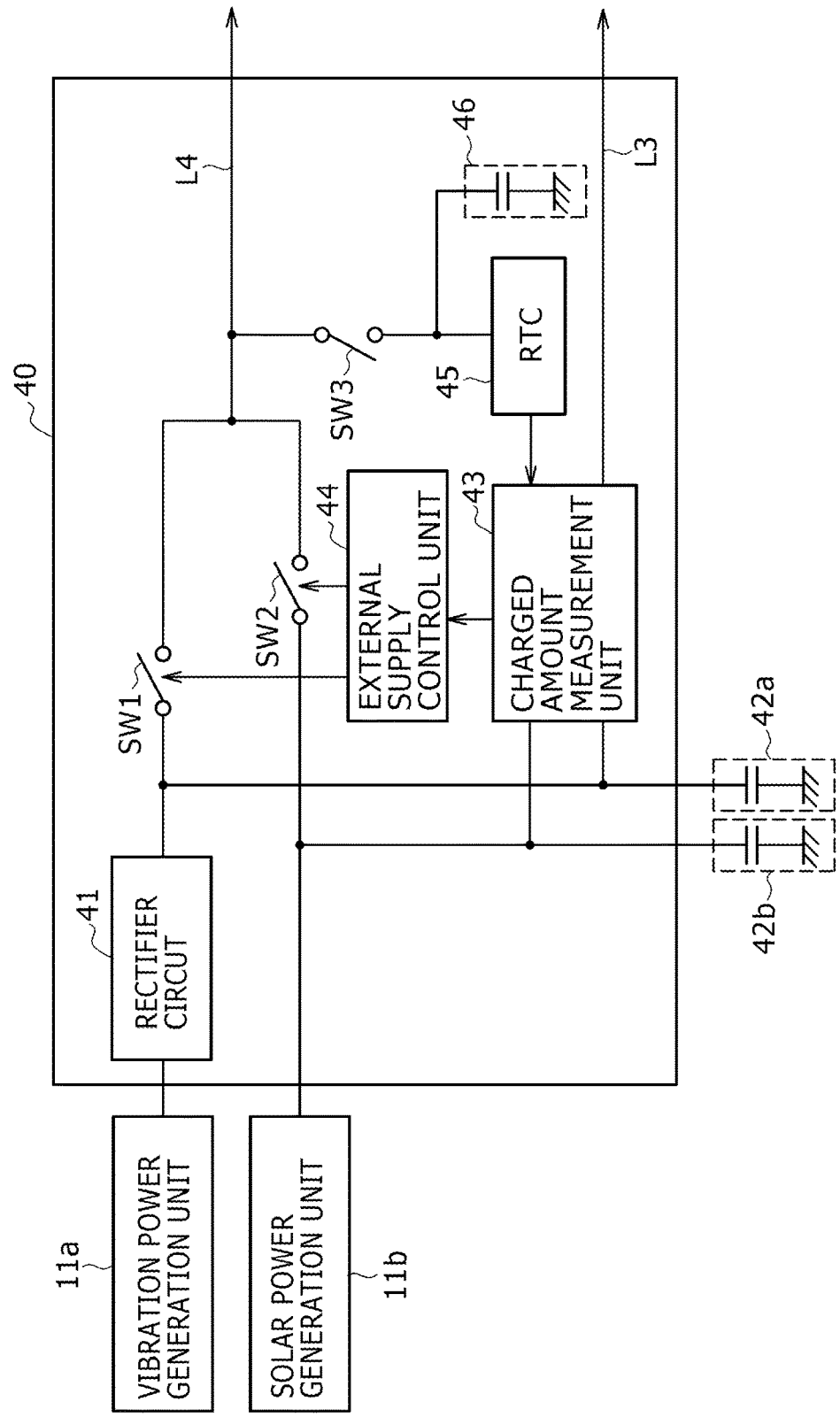
FIG. 15 is a block diagram showing a variation of the power control unit.

FIG. 15 shows the structure of one variation of the power control unit. In connection with the above embodiments, the power generation information was described to be composed of generated electric power and electric energy. Alternatively, the power generation information may be represented by the amount of electric charge accumulated in the electricity storage device. As shown in FIG. 15, a power control unit 40 may be supplied with voltages from the vibration power generation unit 11a and solar power generation unit 11b, for example. A rectifier circuit 41 of the power control unit 40 converts an AC voltage from the vibration power generation unit 11a into a DC voltage. An electricity storage device 42a is charged with the DC voltage fed from the rectifier circuit 41. An electricity storage device 42b is charged with a DC voltage coming from the solar power generation unit 11b.

A charged amount measurement unit 43 is connected to a line between the rectifier circuit 41 and the electricity storage device 42a. The charged amount measurement unit 43 is also connected to a line interposed between the solar power generation unit 11b and the electricity storage device 42b. An RTC 45 is connected to the charged amount measurement unit 43 so that the RTC 45 feeds time information to the unit 43. Using the time information from the RTC 45, the charged amount measurement unit 43 measures the amounts of electric charges (voltages) accumulated in the electricity storage devices 42a and 42b over a predetermined time period. The measured amounts of electric charges are sent to the MCU 12 via a line L3. In this manner, the electricity storage devices may be provided in the power generation unit and the amounts of electric charges in the elements may be used as the power generation information.

The information about the amounts of electric charges measured by the charged amount measurement unit 43 is fed to an external supply control unit 44. The external supply control unit 44 controls ON/OFF of switches SW1 and SW2 in accordance with the amounts of electric charges. For example, if the amount of electric charge in the electricity storage device 42a is large, the external supply control unit 44 turns on the switch SW1 and turns off the switch SW2. If the amount of electric charge in the electricity storage device 42b is large, the external supply control unit 44 turns off the switch SW1 and turns on the switch SW2. The amount of electric charge being large means that the power generation unit connected to the electricity storage device in question is generating a large amount of electric power. Therefore, performing control to turn on and off the switches SW1 and SW2 as mentioned above allows the power generation unit generating a large amount of power to supply the generated power to the outside. The electric power output via the switch SW1 or SW2 is fed onto a line L4 and supplied therethrough to the MCU 12, memory 13, etc.

The RTC 45 is connected with an electricity storage device 46 that supplies electric power to the RTC 45. The electricity storage device 46 is an electric double layer capacitor. The electricity storage device 46 is connected to the line L4 via a switch SW3. When the amount of electric charge in the electricity storage device 46 becomes small, the switch SW3 may be turned on to let the electricity storage device 46 be charged with the voltage from the vibration power generation unit 11a or solar power generation unit 11b.

[Second Variation]

To make the power generation device smaller in size entails reducing the number of power generation units attached to the power generation device. Further, it is difficult to have the power generation device furnished with the wind power generation unit to stipulate the attribute of wind. Taking these points into consideration, in a second variation, power generation information about power generation units not attached to the user's power generation device is acquired from another user, a power generation plant, etc.

Figure 16:
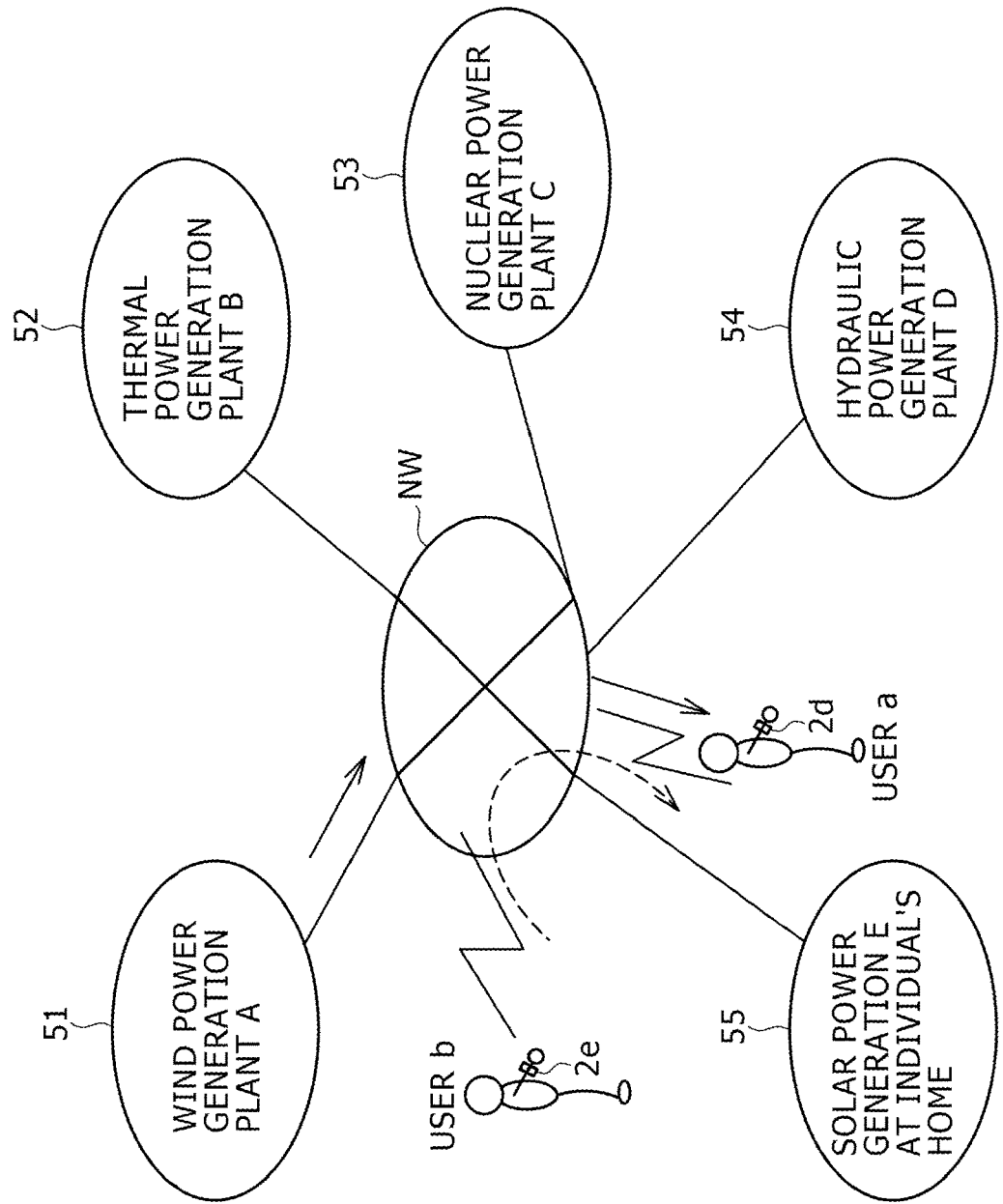
FIG. 16 is a schematic view for explaining another variation.

FIG. 16 outlines typical processing of the second variation. A user "a" owns a power generation device 2d, and a user "b" owns a power generation device 2e. The power generation device 2d has approximately the same structure as the above-described power generation device 2b, except that the power generation device 2d has a solar power generation unit and a vibration power generation unit for example. The power generation device 2e also has approximately the same structure as the above-described power generation device 2b, except that the power generation device 2e has a vibration power generation unit and a radio wave power generation unit for example. The power generation devices 2d and 2e can communicate with each on a network NW when the distance between them becomes shorter than a predetermined distance. Obviously, the power generation devices 2d and 2e may communicate with each other directly without recourse to the network NW.

The power generation device 2d acquires power generation information about power generation units not attached thereto by communication. That is, the power generation device 2d requests the power generation device 2e to transmit the power generation information about the radio wave power generation unit. In response to the request, the power generation device 2e transmits to the power generation device 2d the power generation information about the radio wave power generation unit. Upon identifying the behavior characteristic of the user "a," the power generation device 2d can use the power generation information about the radio wave power generation unit sent from the power generation device 2e.

On the other hand, the power generation device 2e requests the power generation device 2d to transmit the power generation information about the solar power generation unit. In response to the request, the power generation device 2d transmits the power generation information about the solar power generation unit to the power generation device 2e. Upon identifying the behavior characteristic of the user "b," the power generation device 2e can utilize the power generation information about the solar power generation unit sent from the power generation device 2d.

The amount of electric power generated by the vibration power generation unit or by the temperature difference power generation unit varies greatly depending on the user's behavior. By contrast, the amount of electric power generated by the solar power generation unit or by the radio wave generation unit does not vary significantly as long as the units are in a certain proximity. Utilizing such characteristics, the power generation information about the solar power generation unit or radio wave power generation unit is acquired from another user. In this manner, only one of the solar power generation unit and radio wave power generation unit needs to be attached to the power generation device, so that the device can be reduced in size.

Further, power generation information may be acquired not only from other users but also via a network. For example, a business operator may install solar power generation units and radio wave generation units in suitable locations and collect the power generation information from these units in real time. The collected pieces of power generation information about the solar power generation units and radio wave generation units may be uploaded to a server connected with the network NW. When the user transmits his or her position information to the server, the server returns the power generation information about the solar power generation unit and radio wave power generation unit corresponding to the transmitted position information. The user may thus acquire power generation information from the server.

Alternatively, power generation information offered by power generation plants may be utilized. As shown in FIG. 16, power generation plants of different scales are connected to the network NW and the information about the amounts of electric power generated by these plants is disclosed as web information. Naturally, the information about the amounts of generated electric power may be provided not plant by plant but from the website of the electric power company that manages the power generation plants. For example, what may be disclosed on the network NW includes the amount of electric power generated by a wind power generation plant A (reference numeral 51), the amount of power generated by a thermal power generation plant B (reference numeral 52), the amount of power generated by a nuclear power generation plant C (reference numeral 53), the amount of power generated by a hydraulic power generation plant D (reference numeral 54), and the amount of power generated by a solar power generation plant E (reference numeral 55). In addition, a search server, not shown, is connected to the network NW.

The user "a" connects to the search server using the power generation device 2d. The information identifying the power generation device 2d and the position information are then transmitted to the search server. For example, the information identifying the power generation device 2d may be the device ID of the device 2d. As the position information, an IP (Internet Protocol) address, GPS information, and/or information indicative of the direction in which the user is oriented may be utilized. The search server searches for web information in which the power generation information is presented using the ID and position information transmitted from the user. Given IP information of the detected web information, the search server performs IP tracking to acquire the web information about the power generation plant closest to the position of the user "a." The amount of generated electric power found in the acquired web information is transmitted to the power generation device 2d. The power generation device 2d may identify the user's behavior characteristic with use of this supplied amount of generated electric power.

Further, the attributes involved may be varied depending on the user's position and the position of the power generation plant. For example, if the distance between the user and the wind power generation plant A becomes less than a predetermined distance, the wind attribute may be boosted. In addition to the power generation information, information about the building may be reflected in the attributes. For example, while it is difficult to attach a wind power generation unit to the power generation device, power generation information which affects the wind attribute can be acquired by use of information about an amount of electric power generated by a wind power generation plant.

[Third Variation]

The above-described processing may be carried out in groups. The attributes of each group may be reflected in the corresponding character. The character assigned to each group may then be used in competition between the groups. The groups may also be called guilds. FIG. 17 shows how groups are typically constituted. Users 60a through 64a belong to group 1, users 60b through 64b belong to group 2, and users 60r through 65r belong to group "r."

An evaluation index vector S is generated for each group. If it is assumed that "r" stands for a unique number of each group, "m" for the number within each group, and "n" for the number of data record items of a vector Sr, the vector Sr constitutes a matrix of "m" lines and "n" columns. For example, the data records may be power generation information about individual power generation units, and the number of data record items may correspond to the number of power generation units. Thus the evaluation index vector S is generated for each group and transmitted to a server 70.

The server 70 carries out processing using an evaluation function G with regard to the evaluation index vector S. The processing provides an evaluation result vector Q regarding group "r." The evaluation result vector is included in the concept of the behavior characteristic. The character is established based on the evaluation result vector Q. Thus, characters can be set on a group-by-group basis.

The above constitution of the groups is a mere example and may be changed as appropriate. The groups, after being established, may be changed as desired. In a virtual space, users may be grouped beforehand into parties. In the virtual space, the groups may be registered as foes to another. Alternatively, users that are physically close to one another in the real world may be bound as a group. The users physically close to one another in the virtual space may be bound as a group. As a further alternative, the groups of which the characters have the properties similar to one another may be merged into a new group. Upon formation of groups, the user need not necessarily be aware of which group he or she belongs to.

[Other Variations]

In addition to the above-described variations, the embodiments of the present disclosure may be varied variously. For example, the function of the power generation device may be incorporated in a portable electronic apparatus such as a mobile phone or a smartphone. The user's behavior characteristic may also be used as authentication data. For example, a room entry/exit control system may authenticate, in addition to the user's ID, the data about the behavior characteristic unique to each user.

The present disclosure can be applied to a so-called cloud system in which the above-described processes are carried out on a distributed basis. For example, an embodiment of the present disclosure may be used as, in a cloud system that performs a plurality of processes that realize the contents of the present disclosure on a distributed basis with a plurality of apparatuses, one of the apparatuses that performs at least one of the multiple processes. The contents of the processes include, as discussed above in connection with the embodiments, the process of acquiring power generation information, the process of identifying behavior characteristic, the process of getting the behavior characteristic reflected in the virtual object, and the process of displaying information. Further, all processes may be carried out by the power generation device. There may exist a plurality of servers in the above-described embodiments, and the power generation device may function as a server.

It should be understood that the configurations and processes of the embodiments and variations according to the present disclosure may be combined as appropriate so far as no technical problem is caused.

The present disclosure may also be configured as follows:

(1) An identification apparatus including:
an acquisition unit configured to acquire power generation information from a power generation unit; and
an identification unit configured to identify a behavior characteristic in accordance with the power generation information.

(2) The identification apparatus according to (1), including a plurality of power generation units operating different principles of power generation.

(3) The identification apparatus according to (1) or (2), wherein the behavior characteristic is reflected in a virtual object.

(4) The identification apparatus according to (3), wherein the virtual object is generated or an attribute of the virtual object is changed in accordance with the behavior characteristic.

(5) The identification apparatus according to any one of (1) to (4), wherein the appearance of the identification apparatus is changed in accordance with the behavior characteristic.

(6) The identification apparatus according to any one of (1) to (5), further including a communication unit for communication.

(7) The identification apparatus according to (6), wherein the communication unit transmits the behavior characteristic to the outside.

(8) The identification apparatus according to (6) or (7), wherein the communication unit acquires the power generation information from the outside.

(9) The identification apparatus according to any one of (6) to (8), wherein the communication unit acquires the behavior characteristic of another user from the outside.

(10) The identification apparatus according to (9), further including a rewrite unit configured to rewrite the behavior characteristic stored in a storage unit with the behavior characteristic of the other user.

(11) The identification apparatus according to (9), further including an informing unit configured to inform the user that the behavior characteristic of the other user coincides with or approximates the behavior characteristic stored in the storage unit.

(12) A control apparatus including:
an acquisition unit configured to acquire power generation information from a power generation unit; and
an attribute processing unit configured to have the power generation information reflected in an attribute of a virtual object.

(13) An identification method for an identification apparatus, the identification method including:
acquiring power generation information from a power generation unit in the identification apparatus; and
identifying a behavior characteristic in accordance with the power generation information.

(14) A program for causing a computer to execute an identification method including:
acquiring power generation information from a power generation unit; and
identifying a behavior characteristic in accordance with the power generation information.

(15) An identification system having a plurality of the identification apparatuses according to any one of (1) to (11), the identification system including:
acquiring power generation information from each of the identification apparatuses, and
identifying behavior characteristics on a group basis according to the pieces of power generation information.

(16) The identification system according to (15), wherein the behavior characteristic of each of the groups is reflected in a virtual object of each group.

What is claimed is:
1. An identification apparatus comprising:
a processing unit and a memory storing instructions that, when executed by the processing unit, are configured to:
acquire power generation information of a user from a plurality of power generation units operating on different principles of power generation, wherein the plurality of power generation units are associated with the user and wherein the power generation information of the user is representative of power generated by the plurality of power generation units associated with the user;
identify a behavior characteristic of the user in accordance with said power generation information;
change an attribute of a video game character of a video game based on the identified behavior characteristic of the user; and
control the video game character in the video game based on the changed attribute of the video game character.

2. The identification apparatus according to claim 1, wherein said behavior characteristic is reflected in a virtual object.

3. The identification apparatus according to claim 2, wherein said virtual object is generated or an attribute of said virtual object is changed in accordance with said behavior characteristic.

4. The identification apparatus according to claim 1, wherein the appearance of said identification apparatus is changed in accordance with said behavior characteristic.

5. The identification apparatus according to claim 1, further comprising a communication unit.

6. The identification apparatus according to claim 5, wherein said communication unit transmits said behavior characteristic to the outside.

7. The identification apparatus according to claim 5, wherein said communication unit acquires said power generation information from the outside.

8. The identification apparatus according to claim 5, wherein said communication unit acquires the behavior characteristic of another user from the outside.

9. The identification apparatus according to claim 8, wherein the processing unit and the memory are further configured to rewrite said behavior characteristic of the user stored in a storage unit with the behavior characteristic of the other user.

10. The identification apparatus according to claim 8, wherein the processing unit and the memory are further configured to inform the user that the behavior characteristic of the other user coincides with or approximates said behavior characteristic of the user stored in said storage unit.

11. An identification system comprising a plurality of the identification apparatus claimed in claim 1 and a server, the server configured to:
acquire power generation information from each of said identification apparatus, and
identify behavior characteristics on a group basis according to said power generation information.

12. The identification system according to claim 11, wherein the behavior characteristic of each of said groups is reflected in a virtual object of each group.

13. A control apparatus comprising:

a processing unit and a memory storing instructions that, when executed by the processing unit, are configured to:

acquire power generation information of a user from a plurality of power generation units operating on different principles of power generation, wherein the plurality of power generation units are associated with the user and wherein the power generation information of the user is representative of power generated by the plurality of power generation units associated with the user;

reflect said power generation information in an attribute of a virtual object of a video game; and control the virtual object in the video game based on the attribute of the virtual object.

14. An identification method comprising:

acquiring, by an identification apparatus, power generation information of a user from a plurality of power generation units operating on different principles of power generation, wherein the plurality of power generation units are associated with the user and wherein the power generation information of the user is representative of power generated by the plurality of power generation units associated with the user;

identifying a behavior characteristic of the user in accordance with said power generation information;

changing an attribute of a video game character of a video game based on the identified behavior characteristic of the user; and controlling the video game character in the video game based on the changed attribute of the video game character.

15. A computer-readable storage device storing computer-executable instructions that, when executed by a processor, perform an identification method comprising:

acquiring power generation information of a user from a plurality of power generation units operating on different principles of power generation, wherein the plurality of power generation units are associated with the user and wherein the power generation information of the user is representative of power generated by the plurality of power generation units associated with the user;

identifying a behavior characteristic of the user in accordance with said power generation information;

changing an attribute of a video game character of a video game based on the identified behavior characteristic of the user; and controlling the video game character in the video game based on the changed attribute of the video game character.

* * * * *